US006762158B2

(12) United States Patent
Lukenbach et al.

(10) Patent No.: US 6,762,158 B2
(45) Date of Patent: Jul. 13, 2004

(54) PERSONAL CARE COMPOSITIONS COMPRISING LIQUID ESTER MIXTURES

(75) Inventors: Elvin R. Lukenbach, Flemington, NJ (US); Claudia Kaminski, Milford, NJ (US); Sandrine Pascal-Suisse, Rouen (FR); Maurice Tahar, Vernon (FR); Monica Ruggiero, Jackson, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 250 days.

(21) Appl. No.: 09/745,270

(22) Filed: Dec. 21, 2000

(65) Prior Publication Data

US 2002/0035046 A1 Mar. 21, 2002

Related U.S. Application Data

(63) Continuation-in-part of application No. 09/604,563, filed on Jun. 27, 2000.
(60) Provisional application No. 60/141,927, filed on Jul. 1, 1999.

(30) Foreign Application Priority Data

Jun. 23, 2000 (WO) ............................... PCT/US00/17431

(51) Int. Cl.$^7$ .............................................. C11D 10/02
(52) U.S. Cl. ..................... 510/122; 510/119; 510/121; 510/130; 510/136; 510/405; 510/432; 510/437; 510/466
(58) Field of Search ................................ 510/119, 121, 510/122, 130, 136, 405, 437, 432, 466

(56) References Cited

U.S. PATENT DOCUMENTS

| | | | |
|---|---|---|---|
| 4,337,166 A | 6/1982 | Hill et al. ............... 252/174.15 |
| 4,741,855 A | 5/1988 | Grote et al. ................ 252/142 |
| 4,767,625 A | 8/1988 | Mitsuno et al. ............... 424/95 |
| 4,784,844 A | 11/1988 | Thimineur et al. ........... 424/65 |
| 4,980,155 A | 12/1990 | Shah et al. |
| 4,992,477 A | 2/1991 | Geria ........................ 514/782 |
| 5,043,155 A | 8/1991 | Puchalski et al. ............. 424/78 |
| 5,165,917 A | 11/1992 | Zabotto et al. ............... 424/70 |
| 5,217,641 A | 6/1993 | Herstein ..................... 252/171 |
| 5,244,664 A | 9/1993 | Godtfredsen |
| 5,441,667 A | 8/1995 | Tonomura et al. ..... 252/174.15 |
| 5,451,254 A | 9/1995 | Andrean et al. |
| 5,563,031 A | 10/1996 | Yu ................................ 435/4 |
| 5,571,149 A | 11/1996 | Liss et al. ..................... 607/72 |
| 5,599,800 A | 2/1997 | Candau et al. ................ 514/53 |
| 5,622,530 A | 4/1997 | Phipps ........................ 604/20 |
| 5,624,676 A | 4/1997 | Mackey et al. ............. 424/414 |
| 5,661,189 A | 8/1997 | Grieveson et al. .......... 514/784 |
| 5,665,687 A | 9/1997 | Khayat et al. |
| 5,728,389 A | 3/1998 | Sebillotte-Arnaud |
| 5,735,273 A | 4/1998 | Kurnik et al. ............... 128/635 |
| 5,741,766 A | 4/1998 | Marion et al. |
| 5,749,847 A | 5/1998 | Zewert et al. ................ 604/49 |
| 5,756,437 A | 5/1998 | Yamazaki et al. .......... 510/136 |
| 5,766,575 A * | 6/1998 | Crotty et al. ................. 424/59 |
| 5,780,050 A | 7/1998 | Jain et al. .................... 424/449 |
| 5,789,255 A | 8/1998 | Yu ............................... 536/95 |
| 5,791,766 A | 8/1998 | Lee ........................... 362/259 |
| 5,804,540 A | 9/1998 | Tsaur et al. ................. 510/135 |
| 5,814,662 A * | 9/1998 | Znaiden et al. ............. 514/557 |
| 5,827,183 A | 10/1998 | Kurnik et al. .............. 600/345 |
| 5,843,114 A | 12/1998 | Jang .......................... 606/186 |

(List continued on next page.)

FOREIGN PATENT DOCUMENTS

| | | |
|---|---|---|
| EP | 0 295 886 B1 | 12/1988 |
| EP | 0 370 856 B2 | 5/1990 |
| EP | 0 541 347 A2 | 5/1993 |
| EP | 0 651 990 A1 B1 | 5/1995 |
| EP | 0 692 236 B1 | 1/1996 |
| EP | 0 692 240 A1 B1 | 1/1996 |
| EP | 0 705 592 B1 | 4/1996 |
| EP | 0 827 736 A1 | 7/1997 |
| EP | 0 839 521 B1 | 5/1998 |
| GB | 2 250 998 A1 | 6/1992 |
| JP | 20407/88 B2 | 5/1982 |
| JP | 702677 | 1/1995 |
| TW | 79109038 | 8/1991 |
| TW | 79110617 | 6/1992 |
| TW | 79106988 | 7/1992 |
| TW | 050104 | 2/2000 |
| WO | 95/05145 | 2/1995 |
| WO | 95/05160 | 2/1995 |
| WO | 98/35652 A1 | 8/1998 |
| WO | 98/48768 | 11/1998 |
| WO | 98/51276 | 11/1998 |
| WO | 98/52528 A1 | 11/1998 |
| WO | 98/54277 A1 | 12/1998 |
| WO | 98/55576 A1 | 12/1998 |

OTHER PUBLICATIONS

Gollnick, H. et al., "Topical Drug Treatment in Acne", Dermatology, 1998, 196(1), 119–125.

Pierard, G.E. et al., "New Insight into the Topical Management of Excessive Sebum Flow at the Skin Surface," Dermatology, 1998, 196(1), 126–129.

Toyoda, M. et al., "An Overview of Topical Antibiotics for Acne Treatment," Dermatology, 1998, 196(1), 130–134.

Meynadier, J. et al., "Systemic Antibiotics for Acne," Dermatology, 1998, 196(1), 135–139.

Orfanos, C.E. et al, "Oral Retinoids in the Treatment of Seborrhoea and Acne," Dermatology, 1998, 196(1),140–147.

(List continued on next page.)

*Primary Examiner*—Charles Boyer
(74) *Attorney, Agent, or Firm*—Erin M. Harriman

(57) ABSTRACT

Personal care compositions suitable for use in skin care applications, which effectively deliver and/or deposit various benefit agents into and onto the skin and which are relatively non-irritating and thus suitable for use by people having sensitive skin and eyes comprising at least one ester and a water dispersible component.

49 Claims, 8 Drawing Sheets

U.S. PATENT DOCUMENTS

| | | | |
|---|---|---|---|
| 5,865,788 A | | 2/1999 | Edwards et al. ............... 604/22 |
| 5,869,326 A | | 2/1999 | Hofman .................... 435/285.2 |
| 5,871,756 A | * | 2/1999 | Jeffcoat et al. .............. 424/401 |
| 5,888,951 A | | 3/1999 | Gagnebien et al. .......... 510/130 |
| 5,893,885 A | | 4/1999 | Webster, Jr. ................. 607/122 |
| 5,897,553 A | | 4/1999 | Mulier et al. .................. 606/41 |
| 5,906,613 A | | 5/1999 | Mulier et al. .................. 606/41 |
| 5,989,572 A | * | 11/1999 | Habif et al. ................. 424/401 |
| 5,993,434 A | | 11/1999 | Dev et al. .................... 604/501 |
| 6,014,584 A | | 1/2000 | Hofmann et al. ............. 604/21 |
| 6,055,043 A | | 4/2000 | Chambers .................. 356/73.1 |
| 6,063,397 A | | 5/2000 | Fowler et al. ............... 424/443 |
| 6,068,650 A | | 5/2000 | Hofmann et al. .............. 607/2 |
| 6,096,020 A | | 8/2000 | Hofmann .................... 604/501 |
| 6,117,660 A | | 9/2000 | Walters et al. ........... 435/173.6 |
| 6,120,493 A | | 9/2000 | Hofmann .................... 604/506 |
| 6,148,232 A | | 11/2000 | Avrahami .................... 604/20 |
| 6,181,964 B1 | | 1/2001 | Hofmann et al. ............. 604/21 |

OTHER PUBLICATIONS

Beylot, C. et al., "Oral Contraceptives and Cyproterone Acetate in Female Acne Treatment," Dematology, 1998, 196(1), 148–152.

Schmidt, J.B. "Other Antiandrogens", Dermatology, 1998, 196(1), 153–157.

U.S. patent application Ser. No. 09/604,563, Johnson & Johnson Consumer Companies, Inc.

International Search Report PCT/US 00/17431 dated Nov. 17, 2000, WO 01/001949.

U.S. patent application Ser. No. 09/604,449, Johnson & Johnson Consumer Companies, Inc.

* cited by examiner

Retinol Fluorescence 0.3% rol Cleanser

Retinol Fluorescence 0.3% rol Cleanser

Luminosity Change = 78.84

Luminosity Change = 82.33

Rinse off Luminosity Change =37.86

Wiped off Luminosity Change =27.19

Retinol Fluorescence 0.3% rol Cleanser

Retinol Fluorescence 0.3% rol Cleanser

Luminosity Change = 65.92

Luminosity Change = 70.42

Rinse off Luminosity Change =28.97

Wiped off Luminosity Change =17.01

PERSONAL CARE COMPOSITIONS COMPRISING LIQUID ESTER MIXTURES

CROSS REFERENCE TO RELATED APPLICATION

This application is a continuation-in-part of U.S. Ser. No. 09/604,563, filed Jun. 27, 2000, which claims priority to provisional application 60/141,927 filed Jul. 1, 1999. The disclosure of which is hereby incorporated by reference.

BACKGROUND OF THE INVENTION

1. Field of the Invention

This invention relates to compositions suitable for use in personal care applications, and in particular skin care compositions, which effectively deliver and/or deposit various benefit agents into and onto the skin and are relatively non-irritating and thus suitable for use by people having sensitive skin and eyes.

2. Description of the Prior Art

Because of the wide variety of skin, hair and nail problems faced by consumers, consumers have long sought personal care products which can deliver and/or deposit benefit materials that alleviate such problems. In order to be effective, the personal care products must be capable of stabilizing the benefit agent in addition to deliverying and/or depositing the benefit agent. Most delivery systems sacrifice aesthetics in order to achieve stability. Further, because some benefit agents, such as, anti-oxidants, anti-aging materials, are particularly unstable, they may need to be delivered into the outer layers of the skin rather than onto the skin to provide the desired benefit. Thus, not only must the personal care product be capable of stabilizing the benefit agent, but also must be capable of effectively delivering and/or depositing the benefit agent. Furthermore, such products should be of very low irritancy to the skin, in particular where the products are to be used on the face, and even more particularly, in the very sensittive regions surrounding the eyes.

Accordingly, it would be desirable to create such a composition that is capable of deliverying and/or depositing various active agents into and onto the skin. It would also be desirable to create such a composition having a low degree of ocular and skin irritation.

We have surprisingly found that personal care compositions comprising a combination of a water dispersible component and an ester provide the degree of aesthetics and safety to the most sensitive user, while at the same time being a suitable vehicle for delivery skin care benefit materials, including skin-care benefit materials of poor stability.

SUMMARY OF THE INVENTION

In accordance with this invention, there is provided a personal care composition comprising a water dispersible component and an ester.

Another embodiment of this invention is directed to a personal care system comprising:
a. a water dispersible component;
b. an ester;
c. water; and
d. a polymeric emulsifier and/or thickener.

Yet another embodiment of the present invention is directed to a method for making an oil-in water emulsion comprised of:
neutralizing a hydrophilic thickening agent in a hydrophilic phase comprised of a polymeric emulsifier with an effective amount of a neutralizer under conditions sufficient after a lipophilic phase was combined with the hydrophilic phase.

Yet another embodiment of the present invention is directed to a method for making a water-in-oil emulsion comprised of:
neutralizing a hydrophilic thickening agent in a hydrophilic phase comprised of a polymeric emulsifier with an effective amount of a neutralizer under conditions sufficient before combining a lipophilic phase with the hydrophilic phase.

Yet another embodiment of the present invention is directed to a method for depositing benefit agents into and onto the skin comprised of:
topically applying an effective amount of the benefit agent with a composition comprised of an optional liquid silicone, a water dispersible component, and an ester to a desired location.

Yet another embodiment of the present invention is directed to a method for depositing a benefit agent into and/or onto the skin, hair and/or nails comprising applying a composition comprising:
a. an optional liquid silicone;
b. a water dispersible component;
c. an ester;
d. a polymeric emulsifier and/or thickener; and
e. an effective amount of a benefit agent
to a desired location on a human or animal.

The compositions of this invention are capable of effectively delivering and/or depositing various benefit agents into and onto the skin, hair and nails without significantly contributing to ocular irritation.

DESCRIPTION OF THE DRAWINGS

The invention will be more fully understood and further advantages will become apparent when reference is made to the following detailed description of the invention and the accompanying drawing in which.

DETAILED DESCRIPTION OF PREFERRED EMBODIMENTS

Figure 1A:
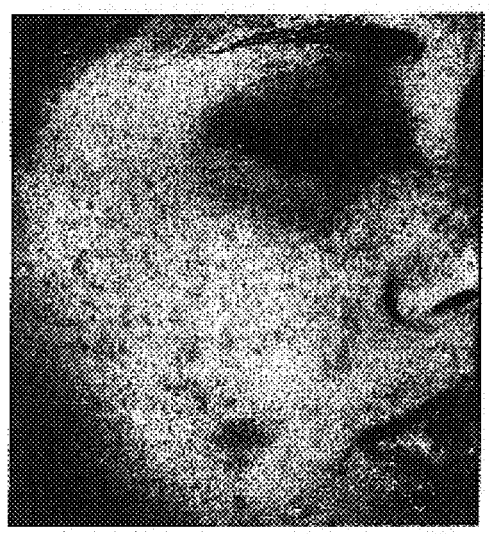
FIGS. 1(a) and (b) are representations that illustrate the right side (FIG. 1(a)) and left side (FIG. 1(b)) of a subject's face prior to treatment as viewed under a CG-395 Filter.

In one embodiment of the present invention, the personal care composition according to the invention may suitably comprise, consist of, or consist essentially of, based upon the total weight of the personal care composition, a) from about 10 percent to about 80 percent, and preferably from about 10 percent to about 45 percent of a water dispersible component; and b) from about 20 percent to about 90 percent, and preferably from 55 percent to about 90 percent of an ester. Generally, the ratio of water dispersible component to ester ranges from about 1:9 to about 4:1, more preferably, from about 1:9 to about 1:1, most preferable from about 1:9 to about 1:3.

The first component of the personal care composition of the present invention is a water dispersible component, which is preferably a water soluble solvent. As used herein, the term "water dispersible component" shall mean a material that produces a uniform, clear or hazy, mixture when combined with at least a weight equivalent of water. Examples of suitable water dispersible components nonexclusively include polyethylene glycol 400, hexylene glycol, propylene glycol, polypropylene glycol-10 methylglucose ether, ethoxydiglycol, polyethylene glycol-6 caprylic/capric glyceride, ethylene glycol monobutyl ether, polyethylene glycol-8 caprylic/capric glycerides, 3-methoxy-3-methyl-1-butanol, dimethyl isosorbide, and mixtures thereof. Most preferred water dispersible components include hexylene glycol, dimethyl isosorbide, polyethylene glycol-6 caprylic/capric glyceride, and mixtures thereof.

The second component of the personal care composition of the present invention is a lipophilic component that preferably is a liquid ester. Preferred esters for use in the composition of this invention include those liquid esters that either possess a structural means for ensuring its liquidity or are heterogeneous in nature. Examples of such structural means include the presence of "interruptions", such as: 1) chain branching; 2) olefinic unsaturation; 3) the presence of either a polyether or a monoalkoxylate in the structure; or 4) the presence of a substituent, e.g. an ethoxylated or propoxylated moiety, bonded between the acid group and the alcohol group. By "heterogeneity," it is meant that the lipophilic component is comprised of a mixture of compounds that vary in the number of carbon atoms in their respective chains.

Examples of suitable esters nonexclusively include:
a) a branched $C_5$ to $C_{22}$ alkyl alcohol ester of an aromatic acid;
b) a straight-chained or branched $C_5$ to $C_{22}$ alkyl acid esters of optionally ethyoxylated/propoxylated polyols having from about 3 carbon atoms to about 7 carbon atoms;
c) branched $C_5$ to $C_{22}$ alkyl alcohol esters of branched polyacids;
d) branched or straight-chained $C_5$ to $C_{22}$ alkyl acid esters of branched and/or unsaturated $C_5$ to $C_{22}$ alkyl alcohols;
e) branched or unsaturated $C_5$ to $C_{22}$ alkyl alcohol esters of an acid selected from the group consisting of adipic acid, succinic acid, maleic acid, sebacic acid, and mixtures thereof
f) polyether interrupted fatty acid esters;
g) benzoic acid ester of heterogeneous alcohols having from about 8 carbon atoms to about 22 carbon atoms; and
h) mixtures thereof,
with straight-chained or branched $C_5$ to $C_{22}$ alkyl acid esters of optionally ethyoxylated/propoxylated polyols, benzoic acid esters of heterogeneous alcohols, and mixtures thereof being particularly preferred.

Suitable branched $C_5$ to $C_{22}$ alkyl alcohol esters of an aromatic acid include those wherein the aromatic acid is benzoic acid. Preferably, the alcohol of this ester is either branched or unsaturated, and may be either a primary alcohol or a secondary alcohol with the former being preferred. Optionally, the aromatic acid may be substituted with hydroxy or alkyl groups having from about 1 carbon atom to about 4 carbon atoms. Specific examples of these esters nonexclusively include, butyloctyl salicylate; hexyldecyl benzoate; and butyloctyl benzoate, which are all available from C.P. Hall Co. under the tradename, "HallStar;" and mixtures thereof, with a mixture of hexyldecyl benzoate and butyloctyl benzoate being particularly preferred.

Another suitable ester includes a straight-chained or branched $C_5$ to $C_{22}$ alkyl acid ester of optionally ethyoxylated/propoxylated polyols, wherein the polyols contain from about 3 carbon atoms to about 7 carbon atoms. Preferably, if the polyol creates a branching point, then the acid group may be straight-chained. Suitable acids used to form these esters typically have from about 8 carbon atoms to about 22 carbon atoms, and preferably from about 8 carbon atoms to about 18 carbon atoms, and most preferably from about 8 carbon atoms to about 12 carbon atoms, and are either saturated or unsaturated, with octanoic acid, capric acid, and mixtures thereof being preferred. Such suitable acids are either straight-chained or branched, and are preferably aliphatic. Suitable polyols used to form these esters typically have from about 3 carbon atoms to about 30 carbon atoms, and preferably from about 3 carbon atoms to about 7 carbon atoms. Examples of such suitable polyols nonexclusively include neopentyl alcohol; polyglycerol, e.g. diglycerol, triglycerol, hexaglycerol, and decaglycerol, wherein the polyglycerol may contain from about 2 to about 10 glycerol groups; glycerin; sorbitan; methyl glucose; trimethylolpropane; and mixtures thereof. Neopentyl alcohol, glycerin, trimethylolpropane, and mixtures thereof are the preferred polyols. Examples of suitable esters nonexclusively include pentaerythritol tetraoctanoate; trimethylolpropane trioctanoate; trioctanoin; pentaerythrityl tetrapelargonate; sorbitan trioleate; caprylic/capric triglyceride; neopentyl alcohol tetraoctanoate, and mixtures thereof, with caprylic/capric triglyceride; pentaerythritol tetraoctanoate; trimethylolpropane trioctanoate; and pentaerythrityl tetrapelargonate being more preferred.

Another suitable ester includes the branched $C_5$ to $C_{22}$ alkyl alcohol esters of branched polyacids such as the tri-esters, tetra-esters, penta-esters, and mixtures thereof. An example of such a polyacid is citric acid. Suitable alkyl alcohols for creating these esters are optionally substituted, e.g., ethoxylated or propoxylated, contain from about 3 carbon atoms to about 22 carbon atoms, and preferably from about 3 carbon atoms to about 8 carbon atoms, and are either straight-chained or branched, with the branching being preferred. These alcohols may either be primary or secondary, and may either be saturated or unsaturated, with saturated being preferred for stability reasons. Specific examples of suitable esters nonexclusively include trioctyldodecyl citrate; triisopropylcitrate; and mixtures thereof.

Another suitable ester includes the branched or straight-chained $C_5$ to $C_{22}$ alkyl acid esters of branched or unsaturated alkyl alcohols wherein the alkyl group of the alcohol has from about 1 carbon atoms to about 18 carbon atoms, and preferably from about 4 carbon atoms to about 10 carbon atoms, provided that the total number of carbon atoms in the ester is at least about 8. Suitable acids for use in making these esters typically have from about 2 carbon atoms to about 22 carbon atoms, and preferably from about 5 carbon atoms to about 10 carbon atoms. However, if the number of acid carbon atoms exceeds the number of carbon atoms in the alcohol, then the acid preferably contains from about 8 carbon atoms to about 18 carbon atoms and the alcohol preferably contains from about 1 carbon atom to about 8 carbon atoms. If the number of acid carbon atoms is less than the number of carbon atoms in the alcohol, then the acid preferably contains from about 2 carbon atoms to about 8 carbon atoms and the alcohol preferably contains from about 8 carbon atoms to about 18 carbon atoms. Preferably, either: 1) the alcohol group or the acid group has branching and/or unsaturation, i.e. both the alcohol and the acid are not straight-chained; or 2) the ester possesses an asymmetrical alkyl distribution. By "asymmetrical alkyl distribution," it is meant that the ester is made from, for example, a short chain alcohol, i.e. having from about 1 carbon atom to about 8 carbon atoms, and a long chain acid, i.e., having greater than about 8 carbon atoms, such as, e.g. butyl stearate, or less preferably the ester is made from, a long chain alcohol, i.e. having greater than about 8 carbon atoms, and a short chain acid, i.e. having from about 1 carbon atom to about 8 carbon atoms. Examples of such suitable esters nonexclusively include tridecyl neopentanoate, isostearyl palmitate, cetyl ricinoleate, cetyl octanoate, isononyl isononanoate, butyl stearate, octyldodecyl soyate, tridecyl erucate, octyldodecyl erucate/eicosil erucate, and mixtures thereof, with cetyl octanoate, isostearyl palmitate, isononyl isononanoate, and mixtures thereof and being preferred.

Another suitable ester includes the branched or unsaturated $C_5$ to $C_{22}$ alkyl alcohol esters of an acid selected from the group consisting of adipic acid, succinic acid, maleic acid, sebacic acid, and mixtures thereof. The alcohol of these esters, which has from about 3 carbon atoms to about 18 carbon atoms, and preferably from about 3 carbon atoms to about 8 carbon atoms, is preferably branched or unsaturated. Examples of such suitable alcohol esters nonexclusively include diisopropyl adipate, dioctyl sebacate, dioctyl succinate, dioctyl maleate, diisostearyl adipate, diethyl sebacate, and mixtures thereof, with diethyl sebacate, dioctyl sebacate, and diisostearyl adipate being preferred.

Another suitable ester includes polyether interrupted fatty acid esters. Examples of such suitable esters nonexclusively include: 1) laureth-2 benzoate; 2) $C_8$ to $C_{22}$ fatty alkyl (optionally polypropylenoxy) polyethyleneoxy carboxylate esters derived from an alcohol having from about 1 carbon atom to about 22 carbon atoms, is either straight or branched, and may contain a phenyl group; and 3) mixtures thereof, with $C_8$ to $C_{22}$ fatty alkyl (optionally polypropylenoxy) polyethyleneoxy carboxylate esters being preferred. Specific examples of preferred esters nonexclusively include isopropyl propylene glycol-2-isodeceth-7 carboxylate, such as "Velsan D8P3" and other commercially available materials sold by Sandoz under the tradename, "Velsan."

Another suitable ester includes the benzoic acid esters of heterogeneous alcohols having from about 8 carbon atoms to about 22 carbon atoms, such as the ester mixtures available from Finetex under the tradename, "Finsolv" and preferably is the $C_{12}$ to $C_{15}$ alcohols benzoate available from Finetex under the tradename, "Finsolv TN."

Preferred combinations of esters include at least one, preferably at least two, and more preferably three of the following esters: a) branched $C_5$ to $C_{22}$ alkyl alcohol esters of an aromatic acid; b) branched or straight-chained $C_5$ to $C_{22}$ alkyl acid esters of branched or unsaturated alkyl alcohols; and c) straight-chained or branched $C_5$ to $C_{22}$ alkyl acid esters of optionally ethyoxylated/propoxylated polyols. In a preferred embodiment, the ester contains, based upon the total weight percent of the esters, from about 30 percent to about 80 percent of branched or straight-chained $C_5$ to $C_{22}$ alkyl acid esters of branched or unsaturated $C_5$ to $C_{22}$ alkyl alcohols; from about 10 percent to about 50 percent of branched $C_5$ to $C_{22}$ alkyl alcohol esters of an aromatic acid; and from about 10 percent to about 50 percent of straight-chained or branched $C_5$ to $C_{22}$ alkyl acid esters of optionally ethyoxylated/propoxylated polyols. In a more preferred embodiment, the ester contains, based upon the total weight percent of the esters, from about 15 percent to about 50 percent isononyl isononanoate, from about 15 percent to about 50 percent isostearyl palmitate, from about 15 percent to about 50 percent cetyl octanoate, and from about 15 percent to about 50 percent pentaerthritol tetraoctanoate.

An optional component of the personal care composition of the present invention is a volatile or nonvolatile liquid silicone, with the former being preferred. The silicone components adds to aesthetics, i.e., less greasy feel, of the compositions according to the invention. Examples of suitable silicones nonexclusively include the polydimethyl siloxanes and derivatives thereof such as hexamethylsiloxane, dimethicone, dimethiconol, and cyclomethicone, with cyclomethicone being preferred. Examples of suitable cyclomethicones nonexclusively include cyclotetradimethyl siloxane; cyclopentadimethyl siloxane, cyclohexadimethyl siloxane, cycloheptadimethyl siloxane, and mixtures thereof. Preferably, the silicone has a viscosity of from about 0.25 cp to about 350 cp.

Another embodiment of the present invention is directed to a personal care system comprising, consisting, or consisting essentially of, based upon the total weight of the personal care system, a) at least about 3 percent and preferably at least about 5 percent of the personal care composition described above; b) from about 70 percent to about 98 percent, and preferably from about 80 percent to about 90 percent of water; c) from about 0.1 percent to 5 percent, preferably, from about 0.5 percent to about 1.5 percent of a polymeric emulsifier, a thickener, or mixture thereof; and optionally e) from about 0.001 percent to about 5 percent of a benefit agent. In one embodiment, the personal care system may comprise, based upon the total weight of the personal care system, from about 0.1 to about 5 percent, and preferably from about 0.5 percent to 1.5 percent of a polymeric emulsifier and/or from about 0.01 percent to about 2 percent, and preferably from about 0.01 percent to about 0.5 percent of a thickener. More preferably, the personal care system contains, based upon the total weight of the personal care system, from about 5 percent to about 30 percent of the personal care composition.

The personal care system may be in the form of an oil-in-water emulsion, a water-in-oil emulsion, or a dispersion.

In addition to the personal care composition, the personal care system is further comprised of polymeric emulsifiers and/or thickeners. As used herein, the term "polymeric emulsifier" shall mean those compounds capable of emulsifying systems whereby the polymeric emulsifiers have a molecular weight of at least about 5000, and preferably are block copolymers having a hydrophilic portion and a hydrophobic portion. When used at amounts effective for emulsifying the personal care system, the polymeric emulsifiers surprisingly do not cause significant eye sting, i.e., when the emulsifer-containing composition was used by 80 consumers in the eye area, no more than about 5% of such users expressed discomfort around the eye area. Examples of suitable polymeric emulsifiers nonexclusively include polyethylene glycol-30 dipolyhydroxystearate available from Uniqema under the tradename, "Arlacel P-135;" dimethicone copolyol, which is available from Goldschmidt Chemical Corporation under the tradename, "Abil EM 90"; substituted acrylates such as those available from The Goodrich Corporation under the tradename, "Pemulen"; and mixtures thereof, with polyethylene glycol-30 dipolyhydroxystearate being preferred.

Examples of suitable hydrophilic thickeners nonexclusively include carbomers available from B.F. Goodrich under the tradename, "Carbopol ETD 2020", acrylate copolymers, hydroxyethylcellulose modified with cetyl ether groups available from Hercules under the tradename, "Natrosol Plus", polyvinylmethyl ether/maleic anhydride (PVM/MA) decadiene crosspolymer available from International Specialty Products under the tradename, "Stabileze QM," and copolymers and mixtures thereof, with carbomers being preferred. Examples of suitable acrylate copolymers nonexclusively include acrylate copolymers available from Rohm & Haas under the tradename, "Aculyn 33," acrylates/aminoacrylates copolymer available from National Starch & Chemical Company under the tradename, "Structure Plus," acrylates/steareth-20 itaconate copolymer available from National Starch & Chemical Company under the tradename, "Structure 2001," acrylates/ceteth-20 itaconate copolymer available from National Starch & Chemical Company under the tradename, "Structure 3001," acrylates/steareth-20 methacrylate copolymer available from Rohm & Haas under the tradename, "Aculyn 22," and copolymers and mixtures thereof.

The personal care system of the present invention may also optionally contain a stability enhancer for the purpose of enhancing the stability of the benefit agent and/or the aesthetics of the personal care system. Generally, the stability enhancer is selected from a nonionic emulsifier, an essentially non-foaming surfactant or mixtures thereof. Examples of suitable nonionic emulsifiers include isocetheth-20, oleth-2, mixture of PEG-40 hydrogenated castor oil and trideceth-9 available from Dragoco Inc. under the tradename, "Dragoco Solubilizer 2/014160," Poloxamer 184, laureth-4, sorbitan trioleate, polyoxyethylene-(2) oleyl ether, sorbitan stearate, cetearyl glucoside, glyceryl oleate, trideceth-9, polyethylene glycol-40 hydrogenated castor oil, and mixtures thereof.

Examples of suitable essentially non-foaming surfactants include non-foaming nonionic surfactants such as sucrose esters, e.g., sucrose cocoate, sucrose stearate and mixtures thereof, with sucrose cocoate being preferred. By "essentially non-foaming," it is meant that the surfactant, when used with the composition of the present invention, has a column height of less than about 20 mm as determined by the Ross-Miles Foam Generation Test. See 18 (I.) Oil & Soap 99–102 (1941)["Ross-Miles Test"), which is incorporated by reference herein. The personal care composition and the personal care system may either be rinseable with water or may be wiped-off. Preferably, the essentially, non-foaming surfactants are used in embodiments wherein the personal care system or the personal care composition is rinseable with water. For example, a preferred combination of hydrophilic components include, based upon the total weight percent of the personal care composition or system, from about 0.1 percent to about 5.0 percent of hexylene glycol, from about 0.5 percent to about 3.0 percent of sucrose cocoate non foaming surfactant, and from about 0.5 percent to about 3.0 percent of polyoxyethylene-6 caprylic/capric triglyceride. An example of a suitable stability enhancer include a mixture of sorbitan stearate and sucrose cocoate available from Uniqema under the tradename, "Arlatone 2121."

When desired, the personal care system contains, based upon the total weight of the personal care system, no more than about 6%, and preferably 5%, of the stability enhancers for cream formulations and no more than about 2%, and preferably no more than 1% of the stability enhancers in thin lotion/milk formulations.

The personal care system and personal care composition may also optionally contain a foaming surfactant. The foaming surfactant may be non-ionic, cationic, amphoteric, or anionic; nonionic surfactants are preferred. By "foaming," it is meant that the surfactant, when used with the composition of the present invention, has a column height of foam greater than about 20 mm as determined by the Ross-Miles Test. As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. Examples of suitable and preferred surfactants may be found in International Patent Application Number WO97/01196, which is incorporated by reference in its entirety herein.

The personal care system and personal care composition may further contain one or more benefit agents or pharmaceutically-acceptable salts thereof. As used herein, the term "benefit agent" includes any active ingredient that is to be delivered into and/or onto the skin, hair or nail at a desired location, such as a cosmetic agent or a pharmaceutical agent. By "cosmetic agent," it is meant any ingredient that is appropriate for cosmetically treating, providing nutrients to, and/or conditioning the hair, nail, and/or skin via topical application. By "pharmaceutical agent," it is mean any drug that is either hydrophobic or hydrophilic in nature and appropriate for topical use. As used herein "medicament agents" include those agents capable of promoting recovery from injury and illness.

The benefit agents useful herein may be categorized by their therapeutic benefit or their postulated mode of action. However, it is to be understood that the benefit agents useful herein may, in some circumstances, provide more than one thereapeutic benefit or operate via greater than one mode of action. Therefore, the particular classifications provided herein are made for the sake of convenience and are not intended to limit the benefit agents to the particular application(s) listed. In addition, the compounds, which are identified below as being suitable for use as benefit agents, may be used in an amount over and above the amount that they may be used for other purposes in the personal care composition or personal care system.

Examples of suitable benefit agents include, but are not limited to, depigmentation agents; reflectants; detangling/wet combing agents; film forming polymers; humectants;

amino acids and their derivatives; antimicrobial agents; allergy inhibitors; anti-acne agents; anti-aging agents; anti-wrinkling agents, antiseptics; analgesics; antitussives; anti-pruritics; local anesthetics; anti-hair loss agents; hair growth promoting agents; hair growth inhibitor agents, antihistamines such as Mandragora Vernalis, Tanacetum Parthenium and the like; antiinfectives such as Acacia Catechu, Aloe Barbadensis, Convallaria Majalis, Echinacea, Eucalyptus, Mentha Piperita, Rosa Canina, Sassafras Albidum, and the like; inflammation inhibitors; anti-emetics; anticholinergics; vasoconstrictors; vasodilators; wound healing promoters; peptides, polypeptides and proteins; deodorants and anti-perspirants; medicament agents; skin emollients and skin moisturizers; skin firming agents, hair conditioners; hair softeners; hair moisturizers; vitamins; tanning agents; skin lightening agents; antifungals such as Centaurea Cyanus, Kalmia Latifolia and antifungals for foot preparations; depilating agents; shaving preparations; external analgesics; perfumes; counterirritants; hemorrhoidals; insecticides; poison ivy products; poison oak products; burn products; anti-diaper rash agents; prickly heat agents; make-up preparations; vitamins; amino acids and their derivatives; herbal extracts; retinoids; flavenoids; sensates; anti-oxidants; skin conditioners; hair lighteners; chelating agents; cell turnover enhancers; coloring agents; pigments; sunscreens, those active ingredients disclosed in U.S. Pat. No. 6,063,397, which is incorporated herein by reference, anti-edema agents, collagen enhancers, and mixtures thereof.

Examples of suitable anti-edema agents nonexclusively include bisabolol natural, synthetic bisabolol, and mixtures thereof.

Examples of suitable vasoconstrictors nonexclusively include horse chestnut extract, prickly ash, and mixtures thereof.

Examples of suitable anti-inflammatory agents nonexclusively include benoxaprofen, centella asiatica, bisabolol, feverfew (whole), feverfew (parthenolide free), green tea extract, green tea concentrate, hydrogen peroxide, lycopene including "Lyc-o-Pen" available from LycoRed Natural Products Industries, Ltd., oat oil, chamomile, and mixtures thereof.

Examples of collagen enhancers nonexclusively include vitamin A, vitamin C, and mixtures thereof.

Examples of suitable skin firming agent nonexclusively include dimethylaminoethanol ("DMAE").

Examples of suitable antipruritics and skin protectants nonexclusively include oatmeal, betaglucan, feverfew, soy and derivatives thereof, bicarbonate of soda, colloidal oatmeal, surfactant based colloidal oatmeal cleanser, Anagallis Arvensis, Oenothera Biennis, Verbena Officinalis, and the like. These antipruritics may be used in an amount, based upon the total weight of the personal care composition, from about 0.01 percent to about 40 percent, and preferably from about 1 percent to about 5 percent.

As used herein, colloidal oatmeal means the powder resulting from the grinding and further processing of whole oat grain meeting United States Standards for Number 1 or Number 2 oats. The colloidal oatmeal has a particle size distribution as follows: not more than 3 percent of the total particles exceed 150 micrometers in size and not more than 20 percent of the total particles exceed 75 micrometers in size. Examples of suitable colloidal oatmeals include, but are not limited to, "Tech-O" available from the Beacon Corporation and colloidal oatmeals available from Quaker.

Examples of suitable reflectants nonexclusively include mica, alumina, calcium silicate, glycol dioleate, glycol distearate, silica, sodium magnesium fluorosilicate, and mixtures thereof.

Suitable detangling/wet combing agents nonexclusively include polyquaternium-10, hydroxypropyltrimonium guar, dioleoylamidoethyl hydroxyethylmonium methosulfate, di-(soyoylethyl) hydroxyethylmonium methosulfate, hydroxyethyl behenamidopropyl dimonium chloride, olealkonium chloride, polyquaternium-47, stearalkonium chloride, tricetylmonium chloride, and mixtures thereof.

Suitable film forming polymers include those that, upon drying, produce a substantially continuous coating or film on the hair, skin, or nails. Nonexclusive examples of suitable film forming polymers include acrylamidopropyl trimonium chloride/acrylamide copolymer; corn starch/acrylamide/sodium acrylate copolymer; polyquaternium-10; polyquaternium-47; polyvinylmethylether/maleic anhydride copolymer; styrene/acrylates copolymers; and mixtures thereof.

Commercially available humectants which are capable of providing moisturization and conditioning properties to the personal care composition are suitable for use in the present invention. The humectant is preferably present in an amount of from about 0 percent to about 10 percent, more preferably from about 0.5 percent to about 5 percent, and most preferably from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, pentylene glycol, dipropylene glycol, and mixtures thereof; 2) polyalkylene glycol of the formula I.:

$$HO-(R''O)_b-H \qquad \text{I.}$$

wherein R" is an alkylene group having from about 2 to about 4 carbon atoms and b is an integer of from about 1 to about 10, such as PEG 4; 3) polyethylene glycol ether of methyl glucose of formula II.:

$$CH_3-C_6H_{10}O_5-(OCH_2CH_2)_c-OH \qquad \text{II.}$$

wherein c is an integer from about 5 to about 25; 4) urea; 5) fructose; 6) glucose; 7) honey; 8) lactic acid; 9) maltose; 10) sodium glucuronate; and 11) mixtures thereof, with glycerine being the preferred humectant.

Suitable amino acid agents include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, capryloyl silk amino acid, capryloyl collagen amino acids; capryloyl keratin amino acids; capryloyl pea amino acids; cocodimonium hydroxypropyl silk amino acids; corn gluten amino acids; cysteine; glutamic acid; glycine; hair keratin amino acids; amino acids such as aspartic acid, threonine, serine, glutamic acid, proline, glycine, alanine, cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof.

Suitable proteins include those polymers that have a long chain, i.e. at least about 10 carbon atoms, and a high molecular weight, i.e. at least about 1000, and are formed by self-condensation of amino acids. Nonexclusive examples of such proteins include collagen, deoxyribonuclease, iodized corn protein; milk protein; protease; serum protein; silk; sweet almond protein; wheat germ protein; wheat protein; alpha and beta helix of keratin proteins; hair proteins, such as intermediate filament proteins, high-sulfur proteins, ultrahigh-sulfur proteins, intermediate filament-associated proteins, high-tyrosine proteins, high-glycine tyrosine proteins, tricohyalin, and mixtures thereof.

Examples of suitable vitamins nonexclusively include vitamin B complex; including thiamine, nicotinic acid, biotin, pantothenic acid, choline, riboflavin, vitamin B6, vitamin B12, pyridoxine, inositol, carnitine; vitamins A,C, D,E,K and their derivatives such as vitamin A palmitate and pro-vitamins, e.g. (i.e. panthenol (pro vitamin B5) and panthenol triacetate) and mixtures thereof.

Examples of suitable antibacterial agents nonexclusively include bacitracin, erythromycin, neomycin, tetracycline, chlortetracycline, benzethonium chloride, phenol, and mixtures thereof.

Examples of suitable skin emollients and skin moisturizers nonexclusively include mineral oil, lanolin, vegetable oils, isostearyl isostearate, glyceryl laurate, methyl gluceth-10, methyl gluceth-20 chitosan, and mixtures thereof.

Examples of suitable hair conditioners nonexclusively include quaternized compounds such as behenamidopropyl PG-dimonium chloride, tricetylmonium chloride, dihydrogenated tallowamidoethyl hydroxyethylmonium methosulfate, and mixtures thereof as well as lipophilic compounds like cetyl alcohol, stearyl alcohol, hydrogenated polydecene, and mixtures thereof.

An example of a suitable hair softener nonexclusively includes silicone compounds, such as those that are either non-volatile or volatile and those that are water soluble or water insoluble. Examples of suitable silicones include organo-substituted polysiloxanes, which are either linear or cyclic polymers of monomeric silicone/oxygen monomers and which nonexclusively include cetyl dimethicone; cetyl triethylammonium dimethicone copolyol phthalate; cyclomethicone; dimethicone copolyol; dimethicone copolyol lactate; hydrolyzed soy protein/dimethicone copolyol acetate; silicone quaternium 13; stearalkonium dimethicone copolyol phthalate; stearamidopropyl dimethicone; and mixtures thereof.

Examples of suitable hair moisturizers nonexclusively include panthenyl ethyl ether, phytantriol, and mixtures thereof.

Examples of sunscreen agents nonexclusively include benzophenones, bornelone, butyl paba, cinnamidopropyl trimethyl ammonium chloride, disodium distyrylbiphenyl disulfonate, paba, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, Padimate O, red petrolatum, and mixtures thereof.

An example of a suitable tanning agent nonexclusively includes dihydroxyacetone.

Examples of skin lightening agents nonexclusively include hydroquinone, catechol and its derivatives, ascorbic acid and its derivatives, and mixtures thereof.

Examples of suitable insecticides (including insect repellents, anti-scabies and anti-lice treatments) nonexclusively include permethrin, pyrethrin, piperonyl butoxide, imidacloprid, N,N-diethyl toluamide, which refers to the material containing predominantly the meta isomer, i.e., N,N-diethyl-m-toluamide, which is also known as DEET; compounds of the formula III.

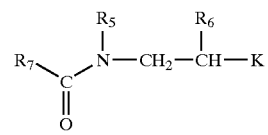

III.

wherein
R$_5$ is a branched or unbranched alkyl group having about 1 to about 6 carbon atoms;
R$_5$ is H, methyl or ethyl;
R$_7$ is a branched or unbranched alkyl or alkoxy group having from about 1 to about 8 carbon atoms; and
K is a —CN or a —COOR$_8$ group, wherein
R$_8$ is a branched or unbranched alkyl group having from about 1 to about 6 carbon atoms,
natural or synthetic pyrethroids, whereby the natural pyrethroids are contained in pyrethrum, the extract of the ground flowers of *Chrysanthemum cinerariaefolium* or *C coccineum*; and mixtures thereof. Within the structure of Formula III. are ethyl 3—(N-butylacetamido)propionate, wherein R$_7$ is a CH$_3$ group, R$_5$ is an n-butyl group, R$_6$ is H, K is COOR$_8$ and R$_8$ is ethyl, which is available commercially from Merck KGaA of Darmstadt, Germany under the name, "Insect Repellent 3535."

An example of an anti fungal for foot preparations nonexclusively includes tolnaftate.

Examples of suitable depilating agents nonexclusively include calcium thioglycolate, magnesium thioglycolate, potassium thioglycolate, strontium thioglycolate, and mixtures thereof.

Examples of suitable external analgesics and local anesthetics nonexclusively include benzocaine, dibucaine, benzyl alcohol, camphor, capsaicin, capsicum, capsicum oleoresin, juniper tar, menthol, methyl nicotinate, methyl salicylate, phenol, resorcinol, turpentine oil, and mixtures thereof.

Examples of suitable antiperspirants and deodorants nonexclusively include aluminium chlorohydrates, aluminium zirconium chlorohydrates, and mixtures thereof.

Examples of suitable counterirritants nonexclusively include camphor, menthol, methyl salicylate, peppermint and clove oils, ichtammol, and mixtures thereof.

An example of a suitable inflammation inhibitor nonexclusively includes hydrocortisone, Fragaria Vesca, Matricaria Chamomilla, and Salvia Officinalis.

Examples of suitable hemorrhoidal products nonexclusively include the anesthetics such as benzocaine, pramoxine hydrochloride, and mixtures thereof; antiseptics such as benzethonium chloride; astringents such as zinc oxide, bismuth subgallate, balsam Peru, and mixtures thereof; skin protectants such as cod liver oil, vegetable oil, and mixtures thereof.

Most preferred benefit agents nonexclusively include DMAE, soy and derivatives thereof, colloidal oatmeal, sulfonated shale oil, olive leaf, elubiol, 6-(1-piperidinyl)-2,4-pyrimidinediamine-3-oxide, finasteride, ketoconazole, salicylic acid, zinc pyrithione, coal tar, benzoyl peroxide, selenium sulfide, hydrocortisone, sulfur, menthol, pramoxine hydrochloride, tricetylmonium chloride, polyquaternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, retinol, erthromycin, tretinoin, and mixtures thereof.

One preferred type of benefit agent includes those therapeutic components that are effective in the treatment of dandruff, seborrheic dermatitis, and psoriasis as well as the symptoms associated therewith. Examples of such suitable benefits agents nonexclusively include zinc pyrithione, anthralin, shale oil and derivatives thereof such as sulfonated shale oil, selenium sulfide, sulfur; salicylic acid; coal tar; povidone-iodine, imidazoles such as ketoconazole, dichlorophenyl imidazolodioxalan, which is commercially available from Janssen Pharmaceutica, N.V., under the tradename, "Elubiol", clotrimazole, itraconazole, miconazole, climbazole, tioconazole, sulconazole, butoconazole, fluconazole, miconazole nitrate and any possible stereo isomers and derivatives thereof; piroctone olamine (Octopirox); selenium sulfide; ciclopirox olamine; anti-psoriasis agents such as vitamin D analogs, e.g. calcipotriol, calcitriol, and tacaleitrol; vitamin A analogs such as esters of vitamin A, e.g. vitamin A palmitate, retinoids, retinols, and retinoic acid; corticosteroids such as hydrocortisone, clobetasone, butyrate, clobetasol propionate and mixtures thereof.

The amount of benefit agent to be combined with the personal care composition or the emulsion may vary depending upon, for example, the ability of the benefit agent to penetrate through the skin, hair or nail, the specific benefit agent chosen, the particular benefit desired, the sensitivity of the user to the benefit agent, the health condition, age, and skin, hair, and/or nail condition of the user, and the like. In sum, the benefit agent is used in a "safe and effective amount," which is an amount that is high enough to deliver a desired skin, hair or nail benefit or to modify a certain condition to be treated, but is low enough to avoid serious side effects, at a reasonable risk to benefit ratio within the scope of sound medical judgment. Unless otherwise expressed herein, typically the benefit agent is present in the personal care composition or personal care system in an amount, based upon the total weight of the composition/system, from about 0.01 percent to about 5.0 percent, and preferably from about 0.01 percent to about 2.0 percent, and more preferably from about 0.01 percent to about 1.0 percent.

Optionally, commercially available detergent thickeners that are capable of imparting the appropriate viscosity to conditioning compositions are suitable for use in this invention. If used, the detergent thickeners should be present in the compositions in an amount sufficient to raise the Brookfield viscosity of the composition to a value of between about 500 to about 10,000 centipoise. Examples of suitable detergent thickeners nonexclusively include: mono or diesters of polyethylene glycol of formula IV.

HO—(CH$_2$CH$_2$O)$_z$H                IV.

wherein z is an integer from about 3 to about 200;
fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. More specifically, suitable detergent thickeners nonexclusively include behenalkonium chloride; cetyl alcohol, quaternium-46, hydroxyethyl cellulose, cocodimonium chloride, polyquaternium-6, polyquaternium-7, quaternium-18, PEG-18 glycerol oleate/cocoate, a mixture of acrylates/steareth-50 acrylate copolymer, laureth-3 and propylene glycol, which is commercially available from Goldschmidt under the tradename "Antil 208," a mixture of cocamidopropylbetaine and glyceryl laurate which is commercially available from Goldschmidt under the tradename, "Antil HS60," a mixture of propylene glycol, PEG 55, and propylene glycol oleate, which is commercially available from Goldschmidt under the tradename, "Antil 414 liquid," and mixtures thereof. Preferred detergent thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

The above described personal care composition and personal care system may be prepared by combining the desired components in a suitable container and mixing them under ambient conditions in any conventional mixing means well known in the art, such as a mechanically stirred propeller, paddle, and the like.

In another preferred embodiment of the personal care system of the present invention wherein a polymeric emulsifier such as, for example, polyethylene glycol-30 dipolyhydroxystearate (hereinafter "PEG 30") or dimethicone copolyol, are used and water is used as the vehicle, an oil-in-water emulsion may be produced. Although both the PEG 30 and dimethicone copolyol are marketed for use in formulating water-in-oil compositions, we have unexpectedly found that oil-in-water emulsions may be created due to the unique processing steps and conditions employed herein. More specifically, we found that when a thickening agent, preferably a hydrophilic thickening agent, is neutralized in the hydrophilic phase of the present invention comprising a polymeric emulsifier prior to adding the lipophilic phase of the present invention thereto, the resulting emulsion is in the form of a water-in-oil emulsion. Conversely, when a thickening agent, preferably a hydrophilic thickening agent, is neutralized in the hydrophilic phase of the present invention comprising a polymeric emulsifier after the lipophilic phase of the present invention is added to the hydrophilic phase, the resulting emulsion is unexpectedly in the form of a oil-in-water emulsion.

Personal care systems of the present invention that are emulsions may contain, based upon the total weight of the emulsion, from about 0.01 percent to about 2 percent, and preferably from about 0.01 percent to about 0.5 percent of hydrophilic thickeners. Suitable neutralizers include any known bases, such as sodium hydroxide, or acids, such as lactic acid, that are capable of neutralizing the hydrophilic thickening agent, in either the hydrophilic phase (if a water-in-oil emulsion is desired) or a mixture of both the hydrophilic phase and the lipophilic phase (if an oil-in-water emulsion is desired) of the present invention to a pH of about 5 to about 7 under ambient temperature. In one embodiment, hydrophilic thickeners including acrylates/aminoacrylates copolymer, acrylates/steareth-20 itaconate copolymer, acrylates/ceteth-20 itaconate copolymer, are preferably neutralized with an acid, such as lactic acid. Hydrophilic thickeners including carbomers, modified hydroxyethylcellulose, polyvinylacetate/maleic anhydride (PVA/MA) decadiene crosspolymer, and acrylates/steareth-20 methacrylate copolymer, are preferably neutralized with a base, such as sodium hydroxide (20%).

In one embodiment, the hydrophilic phase may be comprised of one or more of the following components: water, thickener, stability enhancer, nonfoaming surfactant, and water dispersible component, and the lipophilic phase may be comprised of one or more of the following components: silicone, ester, and polymeric emulsifier.

We have also surprisingly found that the personal care composition and personal care system of the present invention possesses good aesthetic properties without causing any significant ocular discomfort to the user and are particularly suitable for use on the area surrounding the eye. It is well-known in the art that most emulsifiers having a relatively low molecular weight are irritating regardless of their hydrophilic lipophilic balance ("HLB") value. However, we have surprisingly found that when the personal care system of the present invention is produced using the particular polymeric emulsifiers and/or thickeners set forth herein, the resulting composition is gentle and possesses a low degree of ocular and skin irritation.

Another embodiment of the present invention is directed to a method for depositing a benefit agent onto the skin, hair and/or nails comprised of applying either the above-described personal care system or personal care composition with an effective amount of a benefit agent to a desired location on a human or animal. While the frequency and amount of the benefit agent-containing personal care composition/system to be applied will depend upon, for example, the type and amount of benefit agent available, the intended usage of the final composition, i.e. therapeutic versus maintenance regimen, the amount and type of detergent present, and the sensitivity of the individual user to the composition/emulsion, typically the benefit agent-containing personal care composition/system of the present invention should be topically applied to affected body parts at regular intervals, and preferably from about 2 to about 14 times per week. More preferably, the composition/emulsion is applied more frequently during the initial stages of treatment, e.g. from about 5 to about 7 times per week until the desired effect is achieved, then less frequently when maintenance is desired, e.g. from about 2 to about 5 times per week.

We have unexpectedly found that the above-described personal care composition and personal care system are capable of efficiently mediating the deposition and permeation of various benefit agents, such as antidandruff agents, onto and into the skin following topical administration thereto. More specifically, we have surprisingly found that when benefit agents are combined with either the personal care composition or the personal care system of the present invention, the amount of benefit agents deposited onto and/or into the skin, hair, and/or nails is about 50% greater than the amount of benefit agents deposited onto and/or into the skin, hair, and/or nails after application of known, commercial benefit agent-containing compositions.

An alternative preferred embodiment of the present invention is directed to a method for treating hair loss, such as hair loss resulting from alopecia, comprising topically applying the above-described personal care composition/system and the hair loss benefit agent to a desired location on an animal or human, wherein the benefit agent is comprised of an effective amount of a hair loss treatment agent such as minoxidil or mixture thereof. As used herein, "hair loss treatment agents" shall include agents capable of growing hair and/or agents capable of preventing the loss of hair. By "effective amount," it is meant an amount effective for treating hair loss and preferably may range from, based upon the total weight of the personal care system, from about 0.001 percent to about 20 percent, and preferably from about 1 percent to about 5 percent.

Examples of benefit agents suitable for treating hair loss include, but are not limited to potassium channel openers or peripheral vasodilators such as minoxidil, diazoxide, and compounds such as N*-cyano-N-(tert-pentyl)-N'-3-pyridinyl-guanidine ("P-1075") as disclosed in U.S. Pat. No.: 5,244,664, which is incorporated herein by reference; vitamins, such as vitamin E and vitamin C, and derivatives thereof such as vitamin E acetate and vitamin C palmitate; hormones, such as erythropoietin, prostaglandins, such as prostaglandin EI and prostaglandin F2-alpha; fatty acids, such as oleic acid; diruretics such as spironolactone; heat shock proteins ("HSP"), such as HSP 27 and HSP 72; calcium channel blockers, such as verapamil HCL, nifedipine, and diltiazemamiloride; immunosuppressant drugs, such as cyclosporin and Fk-506; 5 alpha-reductase inhibitors such as finasteride; growth factors such as, EGF, IGF and FGF; transforming growth factor beta; tumor necrosis factor; non-steroidal anti-inflammatory agents such as benoxaprofen; retinoids such as tretinoin; cytokines, such as IL-6, IL-1 alpha, and IL-1 beta; cell adhesion molecules such as ICAM; glucorcorticoids such as betametasone; botanical extracts such as aloe, clove, ginseng, rehmannia, swertia, sweet orange, zanthoxylum, Serenoa repens (saw palmetto), Hypoxis rooperi, stinging nettle, pumpkin seeds, and rye pollen; other botanical extracts including sandlewood, red beet root, chrysanthemum, rosemary, burdock root and other hair growth promoter activators which are disclosed in DE 4330597 which is incorporated by reference in its entirety herein; homeopathic agents such as Kalium Phosphoricum D2, Azadirachta indica D2, and Joborandi DI; genes for cytokines, growth factors, and male-pattered baldness; antifungals such as ketoconazole and elubiol; antibiotics such as streptomycin; proteins inhibitors such as cycloheximide; acetazolamide; benoxaprofen; cortisone; diltiazem; hexachlorobenzene; hydantoin; nifedipine; penicillamine; phenothaiazines; pinacidil; psoralens, verapamil; zidovudine; alpha-glucosylated rutin having at least one of the following rutins: quercetin, isoquercitrin, hespeddin, naringin, and methylhesperidin, and flavonoids and transglycosidated derivatives thereof which are all disclosed in JP 7002677, which is incorporated by reference in its entirety herein; and mixtures thereof.

Preferred hair loss treatment agents include minoxidil, 6-(I-piperdinyl)-2,4-pyrimidinediamine-3-oxide, N'-cyano-N-(tert-pentyl)-N'-3-pyridinyl-guanidine, finasteride, retinoids and derivatives thereof, ketoconazole, elubiol or mixtures thereof.

Another embodiment of the present invention is directed to a method for inhibiting hair growth comprising topically applying the above-described personal care composition/system combined with a benefit agent to a desired area on an animal or human for inhibiting hair growth, wherein the benefit agent is comprised of an effective amount of a hair growth inhibiting agent. In a preferred embodiment, the personal care system contains, based upon the total weight of the personal care composition/system, from about 0.001 percent to about 20 percent, and preferably from about 0.01 percent to about 5 percent hair growth inhibiting agent.

Examples of benefit agents suitable for use in inhibiting hair growth include: serine proteases such as trypsin; vitamins such as alpha-tocophenol (vitamin E) and derivatives thereof such as tocophenol acetate and tocophenol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and interferon alpha-2b; retinoids, such as retinol (vitamin A), isotretinoin: glucocorticoids such as betamethasone, and dexamethosone; antihyperlipidaemic drugs, such as triparanol and clofibrate; thallium; mercury; albendazole; allopurinol; amiodarone; amphetamines; androgens; bromocriptine; butyrophenones; carbamazepine; cholestyramine; cimetidine; clofibrate; danazol; desipramine; dixyrazine; ethambutol; etionamide; fluoxetine; gentamicin, gold salts; hydantoins; ibuprofen; imipramine; immunoglobulins; indandiones; indomethacin; intraconazole; levadopa; maprotiline; methysergide; metoprolol; metyrapone; nadolol; nicotinic acid; potassium thiocyanate; propranolol; pyridostimine; salicylates; sulfasalazine; terfenadine; thiamphenicol; thiouracils; trimethadione; troparanol; valproic acid; and mixtures thereof.

Preferred hair growth inhibitory agents include serene proteases, retinol, isotretinoin, betamethoisone, alpha-tocophenol and derivatives thereof, or mixtures thereof.

Another preferred embodiment of the present invention is directed to a method for treating acne and for reducing the signs of aging, i.e. wrinkles, fine lines, and other manifestations of photodamage, comprising topically applying the above-described personal care composition/system and the relevant benefit agent to the skin of an animal or human at a desired area, wherein the benefit agent is comprised of an effective amount of an anti-acne agent or an anti-aging agent, respectively.

Examples of suitable anti-aging agents include, but are not limited to inorganic sunscreens such as titanium dioxide and zinc oxide; organic sunscreens such as octyl-methoxy cinnamates and derivatives thereof; retinoids; vitamins such as vitamin E, vitamin A, vitamin C, vitamin B, and derivatives thereof such as vitamin E acetate, vitamin C palmitate, and the like; antioxidants including beta carotene, alpha hydroxy acids such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, glycolic acid, isopropyl pyruvate, methyl pyruvate, mucic acid, pyruvic acid, saccharic acid, saccaric acid 1,4-lactone, tartaric acid, and tartronic acid; beta hydroxy acids such as beta-hydroxybutyric acid, beta-phenyl-lactic acid, beta-phenylpyruvic acid; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, safflower, and mixtures thereof.

Preferred anti-aging agents include retinoids, antioxidants, alpha-hydroxy acids and beta-hydroxy acid with retinol and tretinoin being most preferred.

Suitable amounts of anti-aging agents include, based upon the total weight of the described personal care composition/system, from about 0.01 percent to about 10 percent, and preferably from about 0.04 percent to about 5 percent.

Examples of suitable anti-acne agents include, but are not limited to topical retinoids (tretinoin, isotretinoin, motretinide, adapalene, tazarotene, azelaic acid, retinol); salicylic acid; benzoyl peroxide; resorcinol; antibiotics such as tetracycline and isomers thereof, erythromycin, and the anti-inflammatory agents such as ibuprofen, naproxen, hetprofen; botanical extracts such as alnus, arnica, artemisia capillaris, asiasarum root, birrh, calendula, chamomile, cnidium, comfrey, fennel, galla rhois, hawthorn, houttuynia, hypericum, jujube, kiwi, licorice, magnolia, olive, peppermint, philodendron, salvia, sasa albo-marginata; imidazoles such as ketoconazole and elubiol, and those described in Gollnick, H et al. 196(I) Dermatology Sebaceous Glands, Acne and Related Disorders, 119–157 (1998), which is incorporated by reference herein, and mixtures thereof.

Preferred anti-acne agents include benzoyl peroxide, retinol, elubiol, antibiotics, and salicylic acid, with retinol and tretinoin being most preferred.

Suitable amount of anti-acne agents include, based upon the total weight of the described personal care system, from about 0.01 percent to about 10 percent, and preferably from about 0.04 percent to about 5 percent.

Another preferred embodiment of the present invention is directed to a method for depigmenting the skin, comprising topically applying to skin at a desired area the above-described personal care composition or system and an effective amount of the depigmentation benefit agent. Suitable effective amounts of depigmentation agents include, based upon the total weight of the described personal care system, from about 0.01 percent to about 10 percent, and preferably from about 0.04 percent to about 5 percent.

Examples of suitable depigmentation agents include, but are not limited to soy and derivatives thereof, retinoids such as retinol; Kojic acid and its derivatives such as, for example, kojic dipalmitate; hydroquinone and it derivatives such as arbutin; transexamic acid; vitamins such as niacin, vitamin C and its derivatives; azelaic acid; placertia; licorice; extracts such as chamomile and green tea, and mixtures thereof, with retinol, Kojic acid, and hydroquinone, being preferred.

An alternative preferred embodiment of the present invention is directed to a method for treating the symptoms and/or the diseases of dandruff, seborrheic dermatitis and/or psoriasis, comprising topically applying the above-described personal care composition or system and the relevant benefit agent to a location desired wherein the benefit agent is comprised of an effective amount of a dandruff treatment agent, a seborrheic dermatitis treatment agent, or a psoriasis treatment agent, respectively. As used herein, "dandruff treatment agent," "seborrheic dermatitis treatment agent," or a "psoriasis treatment agent," respectively, shall include agents capable of treating the symptoms and/or the diseases of dandruff, seborrheic dermatitis, and psoriasis, respectively. By "effective amount," it is meant an amount effective for treating the disease and/or the symptoms associated therewith and preferably may range from, based upon the total weight of the personal care composition or system, from about 0.001 percent to about 10 percent, and preferably from about 0.01 percent to about 5 percent.

Examples of benefit agents suitable for treating the symptoms and/or the diseases of dandruff, seborrheic dermatitis and/or psoriasis, respectively, nonexclusively include those set forth above with shale oil and derivatives thereof, elubiol, ketoconazole, coal tar, salicylic acid, zinc pyrithione, selenium sulfide, hydrocortisone, sulfur, menthol, pramoxine hydrochloride, and mixtures thereof being particularly preferred.

The compositions of the present invention may be directed applied to the skin or may be applied onto other delivery implements such as dry or wet wipes, sponges, brushes, and the like by means known in the art. The compositions may be used in products designed to be left on the skin, wiped from the skin, or rinsed off of the skin.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

Example 1
Preparation of Water-in-Oil Emulsion
Preparation of Lipophilic Phase:

20 g of isostearyl palmitate, available from Brooks Industries, under the tradename "Loronate OP," 20 g of isononyl isononanoate, available from Alzo, Inc. under the tradename, "Wickenol 151,"20 g of cetyl octanoate, available from Brooks Industries, under the tradename "Loronate CIO," 20 g of pentaerythritol tetraoctanoate available from Brooks Industries, under the tradename "Loronate PT," and 20 g of cyclomethicone available from Dow Corning under the tradename, "Dow 345 Fluid" were combined into a glass beaker at a temperature of 25° C. and stirred until homogeneous.

Preparation of Hydrophilic Phase:

Into a primary glass beaker containing 859.7 g of deionized water, 5 g of carbomer available from B.F. Goodrich, Inc. under the tradename, "Carbopol Ultrez" was added thereto with stirring at a temperature of 25° C. until homogenous. Into a separate beaker was added 7.5 g. of sucrose cocoate available from Croda, Inc. under the tradename, "Crodesta SL-40," 7.5 g. of PEG-6 Capric/caprylic glycerides available from Croda, Inc. under the tradename, "Glycerox 767," 10 g of hexylene glycol, 3 g. of methylparaben and 0.5 g of propylparaben with hand stirring until homogeneous to produce a pre-mixture. The pre-mixture was then added to the primary glass beaker with constant stirring until the resulting mixture was homogeneous.

Preparation of Final Composition:

After the 6.8 g. of a 20% aqueous solution of sodium hydroxide was added to the hydrophilic phase with constant stirring at 25° C. until homogeneous, the lipophilic phase was added thereto with stirring at a temperature of 25° C. The resulting mixture was then mixed for 15 minutes.

Example 2
Preparation of Oil-in-Water Emulsion Containing Retinol
Preparation of Lipophilic Phase:

11 g of PEG-30 dipolyhydroxystearate, available from Uniqema, Inc. under the tradename "Arlacel P-135," 50 g of isononyl isononanoate, available from Alzo, Inc. under the tradename, "Wickenol 151," and 50 g of a mixture of hexyldecyl benzoate and butyloctyl benzoate, available from C.P. Hall Company under the tradename, "Hallstar AB" were combined with continous mixing in a vessel and heated to a temperature of 45° C. until homogeneous. After the mixture was cooled to a temperature of 25° C., 50 g of cyclomethicone available from Dow Corning under the tradename, "Dow 344 Fluid" and 6.9 g of a mixture of vitamin A alcohol and polysorbate 20 in a 1:1 weight ratio were added thereto with continuous mixing under an Argon blanket and under yellow light into a glass beaker containing a propeller stirrer until homogeneous. All subsequent procedures with this lipophilic phase were conducted under these conditions of argon blanket and yellow light until the formulation is placed into an oxygen and light impermeable container.

Preparation of Hydrophilic Phase:

Into a primary glass beaker containing 795 g of deionized water, nitrogen was bubbled therein until the subsequent addition of the lipophilic phase thereto so as to minimize exposure to oxygen. 5 g of PEG-8 caprylic/capric glycerides available from Trivent Inc. under the tradename, "Trivasol BW" was then added thereto with stirring at 25° C. until homogeneous. For aiding in dispersion of the thickener in the formulation, 4 g of carbomer available from B.F. Goodrich, Inc. under the tradename, "Carbopol Ultrez" were added to 30 g of dimethylisosorbide available from Uniqema, Inc. under the tradename, "Arlasolve DMI" in a separate beaker with hand stirring. Into the dimethylisosorbide mixture was then added 2 g. of methylparaben and 1 g of propylparaben with hand stirring until homogeneous to produce a pre-mixture. The pre-mixture was then added to the primary glass beaker with constant stirring until the resulting mixture was homogeneous.

Preparation of Final Composition:

The lipophilic phase was then added to the hydrophilic phase with constant stirring at 25° C. until homogeneous. 2 g of triethanolamine available from Union Carbide under the tradename, "Trolamine 99%" was then added to the resulting mixture with stirring until homogeneous. The final emulsion contains the components as set forth in Table E:

TABLE E

Emulsion Components

| Chemical Name | Trade Name | % (wt/wt) |
|---|---|---|
| PEG-30 dipolyhydroxystearate | Arlacel P-135 | 1.1 |
| Isononyl isononanoate | Wickenol | 5.0 |
| Hexyldecyl benzoate and butyloctyl benzoate | Hallstar AB | 5.0 |
| Cyclomethicone | Dow 344 Fluid | 5.0 |
| Vitamin A alcohol and Tween 20 | Retinol 50C | 0.69 |
| Water | Water | 78.81 |
| Carbomer | Carbopol Ultrez | 0.40 |
| PEG-8 caprylic/capric glycerides | Trivasol BW | 0.50 |
| Methylparaben | Methylparaben | 0.20 |
| Propylparaben | Propylparaben | 0.10 |
| Dimethyl isosorbide | Arlasolve DMI | 3.0 |
| Triethanolamine | Trolamine 99% | 0.2 |

Example 3
Preparation of Water-in-Oil Emulsion Containing Retinol
Preparation of Lipophilic Phase:

11 g of PEG-30 dipolyhydroxystearate, available from Uniqema, Inc. under the tradename "Arlacel P-135," 30 g of isononyl isononanoate, available from Alzo, Inc. under the tradename, "Wickenol 151," and 30 g of a mixture of hexyldecyl benzoate and butyloctyl benzoate, available from C.P. Hall Company under the tradename, "Hallstar AB" were combined in a vessel with mixing and heated to a temperature of 45° C. until homogeneous. After the resulting mixture was cooled to a temperature of 25° C., 30 g of cyclomethicone available from Dow Corning under the tradename, "Dow 344 Fluid" and 6.9 g of a mixture of vitamin A alcohol and polysorbate 20 in a 1:1 weight ratio were added thereto with continuous mixing under an Argon blanket and under yellow light into a glass beaker containing a propeller stirrer until homogeneous. All subsequent procedures with this lipophilic phase was conducted under these conditions of argon blanket and yellow light until the formulation is placed into an oxygen and light impermeable container.

Preparation of Hydrophilic Phase:

Into a primary glass beaker containing 863.2 g of deionized water, nitrogen was bubbled therein in order to eliminate dissolved oxygen contained therein. The nitrogen continued to be bubbled therein until the subsequent addition of the lipophilic phase thereto. 5 g of PEG-8 caprylic/capric glycerides available from Trivent Inc. under the tradename, "Trivasol BW" was then added thereto with stirring at 25° C. until homogeneous. For aiding in dispersion of the thickener in the formulation, 4 g of carbomer available from B.F. Goodrich, Inc. under the tradename, "Carbopol Ultrez" were added to 10 g of triisopropyl citrate available from Phoenix Chemical Company under the tradename, "PELEMOL TIPC" in a separate beaker with hand stirring. Into the triisopropyl citrate mixture was then added 2 g. of methylparaben and 1 g of propylparaben with hand stirring until homogeneous to produce a pre-mixture. The pre-mixture was then added to the primary glass beaker with constant stirring until the resulting mixture was homogeneous.

Preparation of Final Composition:

2 g of triethanolamine available from Union Carbide under the tradename, "Trolamine 99%" was then added to the hydrophilic phase with constant stirring at 25° C. until homogeneous. The resulting mixture was then added to the lipophilic phase at constant temperature with stirring until homogeneous. The final emulsion contains the components as set forth in Table F:

TABLE F

Emulsion Components

| Chemical Name | Trade Name | % (wt/wt) |
|---|---|---|
| PEG-30 dipolyhydroxystearate | Arlacel P-135 | 1.1 |
| Isononyl isononanoate | Wickenol | 3.0 |
| Hexyldecyl benzoate and butyloctyl benzoate | Hallstar AB | 3.0 |
| Cyclomethicone | Dow 344 Fluid | 3.0 |
| Vitamin A alcohol and Tween 20 | Retinol 50C | 0.69 |
| Water | Water | 86.320 |
| Carbomer | Carbopol Ultrez | 0.40 |
| PEG-8 caprylic/capric glycerides | Trivasol BW | 1.0 |
| Methylparaben | Methylparaben | 0.20 |
| Propylparaben | Propylparaben | 0.10 |
| Triisopropyl citrate | Pelemol TIPC | 1.0 |
| NaOH | NaOH | 0.190 |

Example 4

Luminosity of the Formulation of Example 2

Figure 1B:
FIGS. 1(c) and (d) are representations that illustrate the right side (FIG. 1(c)) and left side (FIG. 1(d)) of a subject's face while possessing the formulation of Example 2 as viewed under a CG-395 Filter.
FIG. 1(e) is a representation that illustrates the right side of a subject's face after the treatment of Example 2 was rinsed therefrom as viewed under a CG-395 Filter.
FIG. 1(f) is a representation that illustrates the left side of a subject's face after the treatment of Example 2 was wiped therefrom as viewed under a CG-395 Filter.

Digital images of the right side and the left side of a Caucasian woman's face was taken using a digital camera available from Fujix (Model No.: DCS 505) equipped with a 60 mm macro lens under strobe light conditions at F8 and $\frac{1}{125}$ seconds. The camera lens was filtered with a CG-395 filter, and the strobe light source was filtered with a combination of a UG-11 filter and a KG-5 filter. These images are illustrated in FIG. 1(a) and FIG. 1(b), respectively.

Figure 1C:
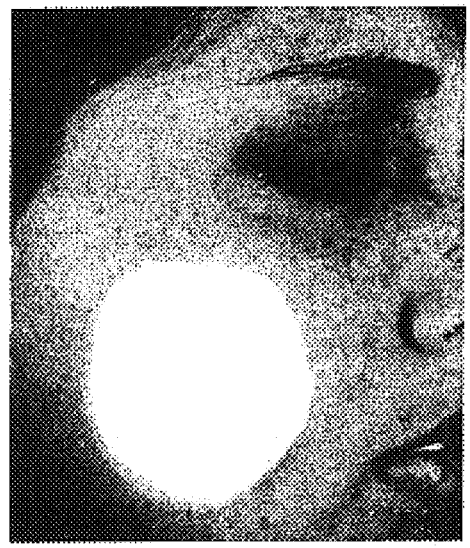
Figure 1D:
Figure 2A:
FIGS. 2(a) and (b) are representations that illustrate the right side (FIG. 2(a)) and left side (FIG. 2(b)) of a subject's face prior to treatment as viewed under a CG-395 Filter.

After approximately 0.09 grams of the 0.3% retinol formulation prepared in Example 10 was applied to about a 20 cm² site on the suborbital (cheek) area of the right side and the left side of the woman's face, digital images were taken thereof under the above conditions as illustrated in FIG. 1(c) and FIG. 1(d), respectively. Using PHOTOSHOP software available from Adobe Inc., the digital image of each site was analyzed for average pixel intensity or luminosity. Luminosity, as used herein, is an indication of brightness of a given area as measured on a scale of 1 to 255, wherein the latter is the most luminescent. Using the 0.3% retinol concentration value, the pixel intensity change, as determined by the difference in pixel intensity between the base surface and the treated surface, for both the treated right side and left side of the face was plotted as a function thereof as illustrated in FIG. 2(a).

Figure 1E:
Figure 1F:

The formulation was then rinsed from the right side of the face, and a digital image was taken of the site under the above conditions as illustrated in FIG. 1(e). The formulation was then wiped twice using a Kimwipe tissue available from Kimberly Clark from the left side of the face, and a digital image was taken of the site under the above conditions as illustrated in FIG. 1(f). The pixel intensity change for the rinsed right side and the wiped left side was plotted on the graph of FIG. 2(a), then the respective deposited retinol concentrations were interpolated therefrom to be 0.145% and 0.1%, respectively.

This Example showed that the formulation of the present invention effectively deposits active agents, such as retinol, onto the skin. A significant amount of the agents remained on the skin after the formulation was removed therefrom. Moreover, this Example highlighted that when the personal care composition of the present invention contains a 0.3% retinol active agent, it deposited the same amount of retinol on the skin as a leave-on product containing 0.145% retinol (when the compositions was removed via rinsing with water) and a leave-on product containing a 0.1% retinol (when the composition was removed via wiping).

Example 5

Luminosity of the Formulation of Example 3

The procedure set forth in Example 4 was repeated using the formulation of Example 3 instead of that of Example 2. The pre-treatment images are illustrated in FIG. 1(a) and FIG. 1(b), respectively.

Figure 2B:
FIGS. 2(c) and (d) are representations that illustrate the right side (FIG. 2(c)) and left side (FIG. 2(d)) of a subject's face while possessing the formulation of Example 2 as viewed under a CG-395 Filter.
FIG. 2(e) is a representation that illustrates the right side of a subject's face after the treatment of Example 2 was rinsed therefrom as viewed under a CG-395 Filter.
FIG. 2(f) is a representation that illustrates the left side of a subject's face after the treatment of Example 2 was wiped therefrom as viewed under a CG-395 Filter.
Figure 2C:
Figure 2D:
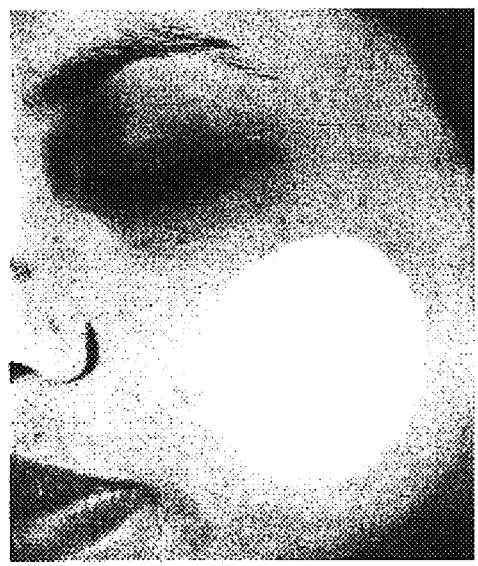
Figure 2E:
Figure 2F:
Figure 3A:
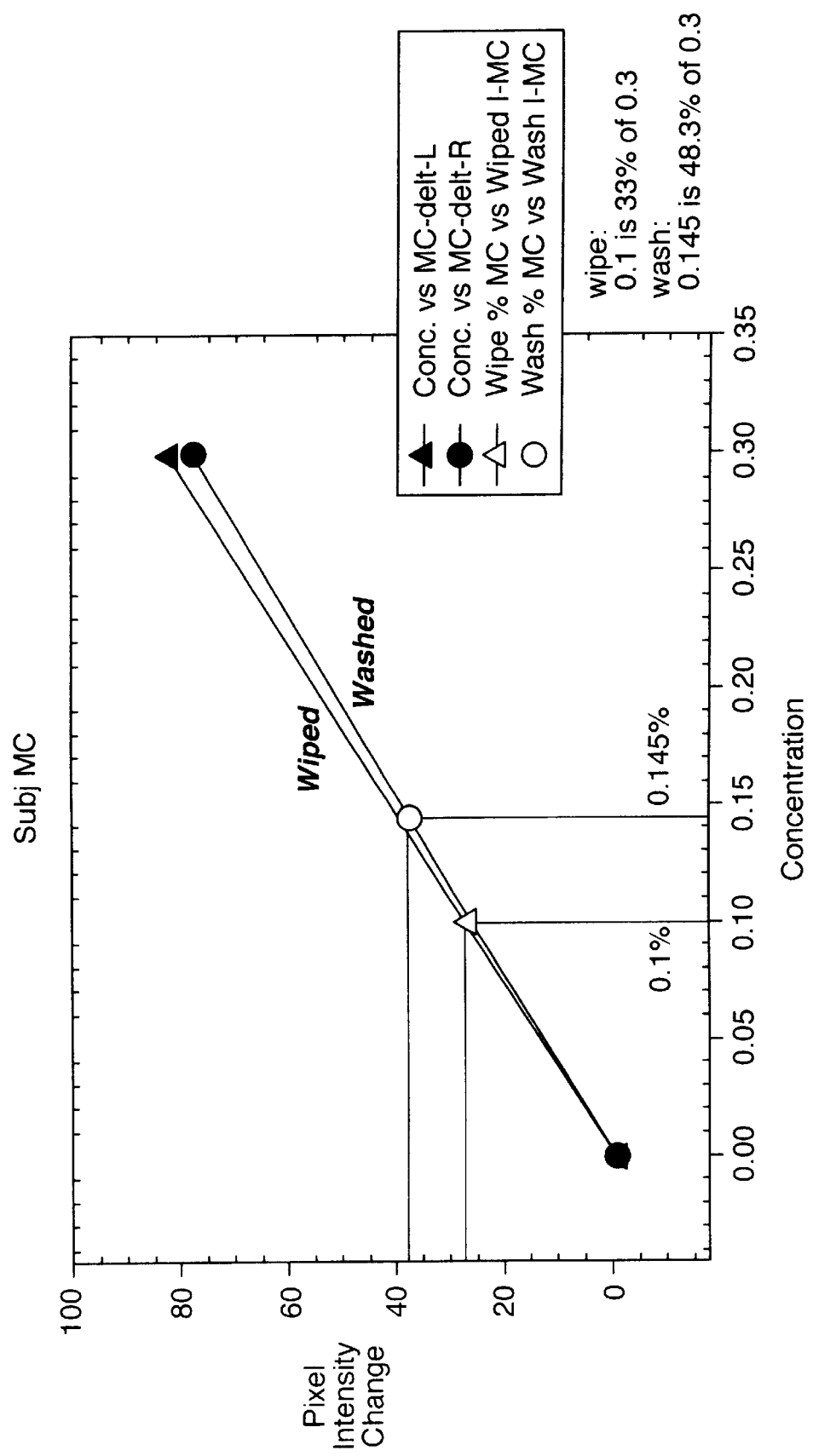
FIG. 3(a) is a graph of concentration of retinol in the formulation of Example 2 versus pixel intensity change.
Figure 3B:
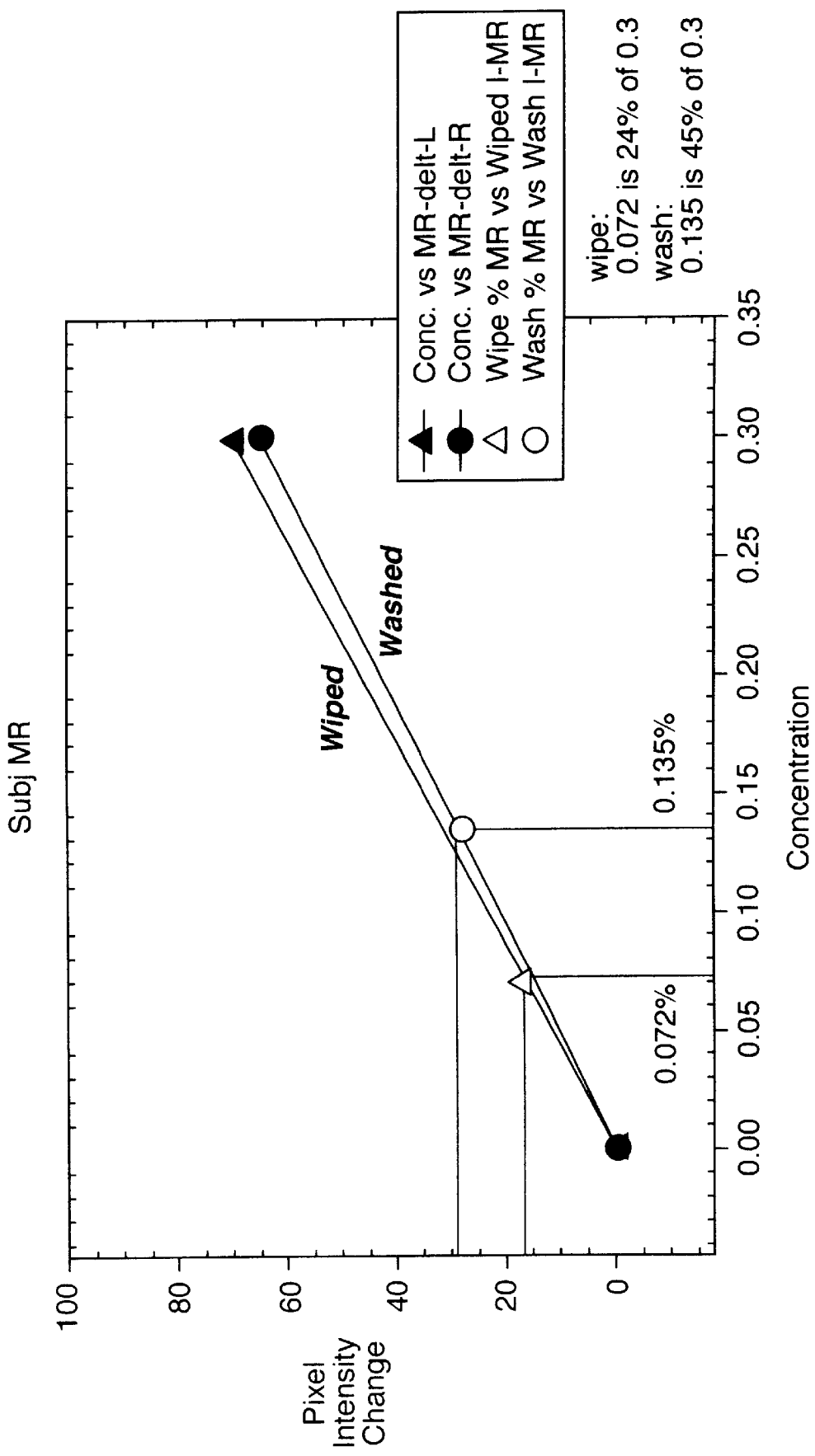
FIG. 3(b) is a graph of concentration of retinol in the formulation of Example 3 versus pixel intensity change.

The formulation-containing images are illustrated in FIG. 1(c) (right side) and FIG. 1 (d) (left side). Using the 0.3% retinol concentration value, the pixel intensity change for the treated right side and left side of the face was plotted as a function thereof as illustrated in FIG. 2(d).

The digital image of the washed site is illustrated in FIG. 1(e), and the image of the wiped side is illustrated in FIG. 1(f). The pixel intensity change for the rinsed right side and the wiped left side was plotted on the graph of FIG. 2(b), then the respective deposited retinol concentrations were interpolated therefrom to be 0.135% and 0.072%, respectively.

This Example showed that the formulation of the present invention effectively deposited active agents, such as retinol, onto the skin. These agents remained present on the skin after the formulation was removed therefrom. Moreover, this Example highlighted that when the personal care composition of the present invention contained a 0.3% retinol active agent, the composition deposited the same amount of retinol on the skin as a leave-on product containing 0.135% retinol (when the compositions was removed via rinsing with water) and a leave-on product containing a 0.072% retinol (when the composition was removed via wiping).

Example 6

Preparation of Oil-in-Water Emulsion Containing DMAE

Preparation of Lipophilic Phase:

10 g of steareth-2 available from Uniqema under the tradename "Brij 72", 8.5 g of isoceteth-20 also available from Uniqema under the tradename "Arlasolve 200", 10 g. of isononyl isononanoate available from Alzo, Inc., under the tradename "Wickenol 151", 10 g. of Isostearyl palmitate available from Brooks Industries under the tradename "Loronate OP", 10 g of cetyl octanoate, available from Brooks Industries, under the tradename "Loronate CIO," 10 g of pentaerythritol tetraoctanoate also available from Brooks Industries, under the tradename "Loronate PT," and 10 g of cyclomethicone available from Dow Corning under the tradename, "Dow 345 Fluid" were combined into a glass beaker at a temperature of 50° C. and stirred until homogeneous.

Preparation of Hydrophilic Phase:

602.5 g of deionized water were weighed into a primary glass beaker and heated to 78–82° C. With constant agitation, 4 g of PVM/MA Decadiene Crosspolymer available from ISP under the tradename, "Stabileze QM" was added thereto and held at 78–82° C. until homogenous. This mixture was then cooled to 40–50° C., during which time, 1 g. of disodium EDTA, 10 g. of hexylene glycol, 7.5 g. of PEG-6 caprylic/capric glycerides available from Croda, Inc. under the tradename, "Glycerox 767", and 10 g. of PEG-150 pentaerythrityl tetrastearate also available from Croda under the tradename, "Crothix Liquid," were added to the primary beaker with constant stirring.

Preparation of Final Composition:

When both the lipophilic phase and the hydrophilic phase were at a temperature of 40° C.–50° C., the lipophilic phase was added to the hydrophilic phase with constant stirring. In a separate beaker, 30 g. of 2-(dimethylamino) ethanol, available from BASF under the tradename DMAE, and 50 g. of L-tyrosine available from Ajinimoto under the tradename "L-Tyrosine" were added to 150 g. of water, and mixed until homogenous. This premix was then added to the primary beaker with constant stirring. 10 g of Nylon-12 available from Kobo Products, Inc., under the tradename "SP-10", 5 g of talc available from Luzenac America under the tradename, "Windsor Talc 66", 10 g of silicone quaternium-13 available from Biosil Industries under the tradename, "Biosil Basics SPQ," and 10 grams of a phenoxyethanol, methylparaben, butylparaben, ethylparaben and propylparaben solution available from Nipa under the tradename "Phenonip" were added separately to the primary beaker with constant stirring. The entire mixture was adjusted to a pH of 7.0–7.5 with a 70% aqueous solution of glycolic acid, and homogenized for 2 minutes at medium power with a Gifford-Wood homogenizer.

After about 1 ml to about 10 ml of the resulting formulation is applied to the facial skin of consumers, the consumers perceive that their facial skin appears and feels firmer and "lifted."

Example 7

Preparation of Oil in Water Emulsion Containing a Polymeric Emulsifier and Colloidal Oat Flour Preparation of Hydrophilic Phase:

Into a primary glass beaker containing 850.70 g of deionized water, 10 g of Colloidal Oat Flour available from Quaker was added thereto with stirring at 25° C. until a homogeneous, smooth slurry was achieved. 2.5 g. of Acrylates/C10–30 Alkyl Acrylate Crosspolymer available from B.F. Goodrich, Inc. under the tradename, "Pemulen TR-1" and 2.5 g. of Carbomer, also available from B.F. Goodrich, Inc. under the tradename "Carbopol Ultrez" were then added to the primary beaker and mixed with slower agitation until homogenous. Into a separate beaker was added 7.5 g. of sucrose cocoate available from Croda, Inc. under the tradename, "Crodesta SL-40," 7.5 g. of PEG-6 Capric/caprylic glycerides available from Croda, Inc. under the tradename, "Glycerox 767," 10 g of hexylene glycol, 3 g. of methylparaben and 0.5 g of propylparaben with hand stirring until homogeneous to produce a pre-mixture. The pre-mixture was then added to the primary glass beaker with constant stirring until the resulting mixture was homogeneous.

Preparation of Final Composition:

20 g of isostearyl palmitate, available from Brooks Industries, under the tradename "Loronate OP," 20 g of isononyl isononanoate, available from Alzo, Inc. under the tradename, "Wickenol 151," 20 g of cetyl octanoate, available from Brooks Industries, under the tradename "Loronate CIO," 20 g of pentaerythritol tetraoctanoate available from Brooks Industries, under the tradename "Loronate PT," and 20 g of cyclomethicone available from Dow Corning under the tradename, "Dow 345 Fluid" were each added separately to the primary beaker with constant stirring at 25° C. until homogeneous. 2.5 g of Tetrasodium EDTA and, 6.8 g. of a 20% aqueous solution of sodium hydroxide was then added thereto with stirring at a temperature of 25° C. The resulting mixture was then mixed for 15 minutes.

Example 8

Preparation of Oil in Water Emulsion Containing a Polymeric Emulsifier and Colloidal Oat Flour Preparation of Preservative Pre-Blend 4 g of methylparaben, 1 g of propylparaben, 7.5 g of PEG-6 capric/caprylic glycerides available from Croda, Inc. under the tradename, "Glycerox 767," 7.5 g of sucrose cocoate also available from Croda, Inc. under the tradename, "Crodesta SL-40," and 10 g of hexylene glycol were combined with mixing under ambient conditions until homogeneous.

Preparation of Emulsion:

Into a primary glass beaker containing 852.5 g of Purified Water (USP), 10 g of Colloidal Oat Flour available from Quaker were added thereto with stirring at about 200 rpm and a temperature of about 20° C. to about 30° C. until a homogeneous, smooth slurry was achieved. 2.5 g. of Acrylates/C10–30 Alkyl Acrylate Crosspolymer available from B.F. Goodrich, Inc. under the tradename, "Pemulen TR-1" and 2.5 g. of Carbomer, also available from B.F. Goodrich, Inc. under the tradename "Carbopol Ultrez" were then added thereto and mixed with slower agitation until homogenous. After adding the Preservative Pre-blend with increased mixing at about 200 rpm thereto, the following components were sequentially added thereto with constant stirring at about 20° C. to about 30° C. until homogeneous, with intervals of 5 minutes between the addition of each respective component: 20 g of isononyl isononanoate, available from Alzo, Inc. under the tradename, "Wickenol 151," 20 g of cyclomethicone available from Dow Corning under the tradename, "Dow 345 Fluid", 20 g of isostearyl palmitate, available from Brooks Industries, under the tradename "Loronate OP," 20 g of cetyl octanoate, available from Brooks Industries, under the tradename "Loronate CIO," 20 g of pentaerythritol tetraoctanoate available from Brooks Industries, under the tradename "Loronate PT." 2.5 g of Tetrasodium EDTA and enough of a a 20% aqueous solution of sodium hydroxide was then added thereto with stirring at a temperature of about 20° C. to about 30° C. to produce a final mixture having a pH of 5.9 to 6.5. The resulting mixture was then mixed until homogeneous.

Example 9

Preparation of Oil-in-Water Emulsion with Non-Ionic Emulsifier

Preparation of Lipophilic Phase:

20 g of isostearyl palmitate, available from Brooks Industries, under the tradename "Loronate OP," 20 g of isononyl isononanoate, available from Alzo, Inc. under the tradename, "Wickenol 151," 20 g of cetyl octanoate, available from Brooks Industries, under the tradename "Loronate CIO," 20 g of pentaerythritol tetraoctanoate available from Brooks Industries, under the tradename "Loronate PT," were combined into a glass beaker at a temperature of 25° C. and stirred until homogeneous.

Preparation of Hydrophilic Phase:

Into a primary glass beaker containing 859.7 g of deionized water, 2 g of carbomer available from B.F. Goodrich, Inc. under the tradename, "Carbopol ETD 2020", and 1 g of C10–C30 alkyl acrylate/crosspolymer commercially available from B.F. Goodrich under the tradename, "Pemulen TR1" were added thereto with stirring at a temperature of 25° C. until dispersed. While heating the mixture to 75° C., 1.2 g of tromethamine, 1 g of EDTA, 7.5 g. of PEG-6 Capric/caprylic glycerides available from Croda, Inc. under the tradename, "Glycerox 767," 10 g of hexylene glycol, 4 g. of methylparaben and 1 g of propylparaben were added with constant stirring until the resulting mixture was homogeneous. After the mixture reached a temperature of 75° C., 10 g. of a mixture of sorbitan stearate and sucrose cocoate available from Uniqema under the tradename, "Arlatone 2121," were added thereto with stirring for 30 minutes at constant temperature.

Preparation of Final Composition:

After the lipophilic phase was heated to a temperature of 75° C., it was then added to the hydrophilic phase with constant stirring at 75° C. until homogeneous. After the mixture was then cooled to 35° C., 20 g of cyclomethicone available from Dow Corning under the tradename, "Dow 345 Fluid" was added thereto. After the mixture was cooled to 25° C., 0.4 g. of tromethamine was then added thereto with stirring at constant temperature such that the resulting mixture had a pH of 5.5.

Example 10
Preparation of Personal Care Composition 20 g of cyclomethicone available from the Dow Corning Corporation under the tradename, "DOW CORNING 345," 15 g of hexylene glycol, and 65 g of a mixture of hexyl decyl benzoate and butyl octyl benzoate available from the C.P. Hall Company under the tradename, "Hallstar AB" are sequentially added to a vessel with mixing at about 100 rpm under ambient conditions until the final mixture is homogeneous.

About 1 ml to about 10 ml of the resulting personal care composition may be applied to the skin as a leave-on composition without the need for rinsing.

We claim:

1. A personal care composition comprising:
   a. from about 10 percent to about 80 percent, based upon the total weight of the composition of at least two water dispersible components selected from water dispersible components that when combined with at least a weight equivalent of water produces (i) a uniform clear mixture or (ii) uniform hazy mixture; and
   b. from about 55 percent to about 90 percent, based upon the total weight of the composition of at least two liquid esters selected from the group consisting of (i) liquid esters that possess a structural means for ensuring the liquidity of the ester; and (ii) heterogeneous esters.

2. The personal care composition of claim 1, wherein the ratio of water dispersible components to esters ranges from about 1:9 to about 4:1.

3. The personal care composition of claim 1, further comprising a silicone component.

4. The personal care composition of claim 1, wherein the at least two water dispersible components comprise at least one water dispersible component selected from the group consisting of polyethylene glycol 400, hexylene glycol, propylene glycol, polypropylene glycol-10 methylglucose ether, ethoxydiglycol, polyethylene glycol-6 caprylic/capric glycendes, ethylene glycol monobutyl ether, triisopropyl citrate, polyethylene glycol-8 caprylic/capric glycerides, 3-methoxy-3-methyl-1-butanol, dimethyl isosorbide, and polyethylene-6 caprylic/capric triglyceride.

5. The personal care composition of claim 4, wherein the at least two water dispersible components comprise at least one water dispersible component selected from the group consisting of hexylene glycol, dimethyl isosorbide, and polyethylene glycol-6 caprylic/capric glyceride.

6. The personal care composition of claim 1, wherein the at least two water dispersible components comprise, based upon the total weight percent of the personal care composition,
   a) from about 5 percent to about 15 percent of hexylene glycol;
   b) from about 5 percent to about 10 percent of polyethylene-6 caprylic/capric triglyceride.

7. The personal care composition of claim 1, wherein the at least two esters comprise at least one ester selected from the group consisting of
   a) a branched $C_5$ to $C_{22}$ alkyl alcohol ester of an aromatic acid;
   b) a straight-chained or branched $C_5$ to $C_{22}$ alkyl acid esters of optionally ethyoxylated/propoxylated polyols having from about 3 carbon atoms to about 7 carbon atoms;
   c) branched $C_5$ to $C_{22}$ alkyl alcohol esters of branched polyacids;
   d) branched or straight-chained $C_5$ to $C_{22}$ alkyl acid esters of branched and/or unsaturated $C_5$ to $C_{22}$ alkyl alcohols;
   e) branched or unsaturated $C_5$ to $C_{22}$ alkyl alcohol esters of an acid selected from the group consisting of adipic acid, succinic acid, sebacic acid, maleic acid, and mixtures thereof
   f) polyether interrupted fatty acid esters; and
   g) benzoic acid ester of heterogeneous alcohols having from about 8 carbon atoms to about 22 carbon atoms.

8. The personal care composition of claim 7, wherein the at least two esters comprise at least one ester selected from the group consisting of straight-chained or branched $C_5$ to $C_{22}$ alkyl acid esters of optionally ethyoxylated/propoxylated polyols; and benzoic acid esters of heterogeneous alcohols.

9. The personal care composition of claim 7, wherein the at least two esters comprise at least one ester selected from the group consisting of butyloctyl salicylate; hexyldecyl benzoate; and butyloctyl benzoate; and alkyl benzoates having from about 12 carbon atoms to about 15 carbon atoms.

10. The personal care composition of claim 9, wherein the at least two esters comprise at least one ester selected from the group consisting of hexyldecyl benzoate, and butyloctyl benzoate.

11. The personal care composition of claim 7, wherein the at least two esters comprise at least one ester selected from the group consisting of pentaerythritol tetraoctanoate; trimethylolpropane trioctanoate; trioctanoin; pentaerythrityl tetrapelargonate; sorbitan trioleate; caprylic/capric triglyceride; and neopentyl alcohol tetraoctanoate.

12. The personal care composition of claim 11, wherein the at least two esters comprise at least one ester selected from the group consisting of caprylic/capric triglyceride; pentaerythritol tetraoctanoate; trimethylolpropane trioctanoate; pentaerythrityl tetrapelargonate.

13. The personal care composition of claim 7, wherein the at least two esters comprise at least one ester selected from the group consisting of branched alkyl alcohol esters of branched polyacids, wherein the alkyl alcohol is optionally substituted and contains from about 3 carbon atoms to about 22 carbon atoms.

14. The personal care composition of claim 13, wherein the at least two esters comprise trioctyldodecyl citrate.

15. The personal care composition of claim 7, wherein the at least two esters comprise at least one ester selected from the group consisting of tridecyl neopentanoate, isostearyl palmitate, cetyl ricinoleate, cetyl octanoate, isononyl isononanoate, butyl stearate, octyldodecyl soyate, tridecyl erucate, octyldodecyl erucate/eicosil erucate, and mixtures thereof.

16. The personal care composition of claim 15, wherein the at least two esters comprise at least one ester selected from the group consisting of cetyl octanoate, isostearyl palmitate, isononyl isononanoate, and mixtures thereof.

17. The personal care composition of claim 7, wherein the at least two esters comprise at least one ester selected from the group consisting of diisopropyl adipate, dioctyl sebacate, dioctyl succinate, dioctyl maleate, diisostearyl adipate, diethyl sebacate, and mixtures thereof.

18. The personal care composition of claim 17, wherein the at least two esters comprise at least one ester selected from the group consisting of diethyl sebacate, dioctyl sebacate, diisostearyl adipate, and mixtures thereof.

19. The personal care composition of claim 7, wherein the at least two esters comprise at least one ester selected from the group consisting of laureth-2 benzoate; and $C_8$ to $C_{22}$ fatty alkyl (optionally polypropylenoxy) polyethyleneoxy carboxylate esters derived from an alcohol having from about 1 carbon atom to about 22 carbon atoms.

20. The personal care composition of claim 19, wherein the at least two esters comprise isopropyl propylene glycol-2-isodeceth-7 carboxylate.

21. The personal care composition of claim 7, wherein the at least two esters are selected from at least two of the following esters:
   a) branched $C_5$ to $C_{22}$ alkyl alcohol esters of an aromatic acid;
   b) branched or straight-chained $C_5$ to $C_{22}$ alkyl acid esters of branched or unsaturated $C_5$ to $C_{22}$ alkyl alcohols; and
   c) straight-chained or branched $C_5$ to $C_{22}$ alkyl acid esters of optionally ethyoxylated/propoxylated polyols.

22. The personal care composition of claim 7, wherein the at least two esters comprise, based upon the total weight percent of the esters,:
   a) from about 30 percent to about 80 percent of branched or straight-chained $C_5$ to $C_{22}$ alkyl acid esters of branched or unsaturated $C_5$ to $C_{22}$ alkyl alcohols;
   b) from about 10 percent to about 50 percent of branched $C_5$ to $C_{22}$ alkyl alcohol esters of an aromatic acid; and
   c) from about 10 percent to about 50 percent of straight-chained or branched $C_5$ to $C_{22}$ alkyl acid esters of optionally ethyoxylated/propoxylated polyols.

23. The personal care composition of claim 7, wherein the at least two esters comprise, based upon the total weight percent of the ester,:
   a) from about 15 percent to about 50 percent isononyl isononanoate;
   b) from about 15 percent to about 50 percent isostearyl palmitate;
   c) from about 15 percent to about 50 percent cetyl octanoate; and
   d) from about 15 percent to about 50 percent pentaerythritol tetraoctanoate.

24. A personal care system comprising:
   a. the personal care composition of claim 1;
   b. water; and
   c. a polymeric emulsifier and/or a thickener.

25. The personal care system of claim 24 comprising, based upon the total weight of the personal care system:
   a. at least about 3 percent of the personal care composition of claim 1;
   b. from about 70 percent to about 98 percent of water; and
   c. from about 0.5 to about 1.5 percent of a polymeric emulsifier and/or thickener.

26. The personal care system of claim 24, wherein the polymeric emulsifier is polyethylene glycol-30 dipolyhydroxystearate; dimethicone copolyol; substituted acrylates; and mixtures thereof.

27. The personal care system of claim 24, wherein the thickener is selected from the group consisting of carbomers, acrylate copolymers, hydroxyethylcellulose modified with cetyl ether groups, polyvinylmethyl ether/maleic anhydride (PVM/MA) decadiene crosspolymer, and mixtures thereof.

28. The personal care system of claim 24, wherein the thickener is selected from the group consisting of acrylates/aminoacrylates copolymer, acrylateslsteareth-20 methacrylate copolymer; acrylates/ceteth-20 itaconate copolymer, acrylates/steareth-20 itaconate copolymer, carbomers, modified hydroxycellulose, polyvinylacetate/maleic anhydride (PVA/MA) decadiene crosspolymer, and mixtures thereof.

29. The system of claim 28, further comprising a benefit agent.

30. The system of claim 29, wherein the benefit agent is selected from the group consisting of vasoconstrictors, collagen enhancers, anti-edema agents, depigmentation agents; reflectants; detangling/wet combing agents; film forming polymers; humectants; amino acid agents; antimicrobial agents; allergy inhibitors; anti-acne agents; anti-aging agents; anti-wrinkling agents, antiseptics; analgesics; antitussives; antipruritics; local anesthetics; anti-hair loss agents; hair growth promoting agents; hair growth inhibitor agents; antihistamines; antiinfectives; inflammation inhibitors; anti-emetics; anticholinergics; vasoconstrictors; vasodilators; wound healing promoters; peptides, polypeptides and proteins; deodorants and anti-perspirants; medicament agents; skin emollients and skin moisturizers; skin firming agents, hair conditioners; hair softeners; hair moisturizers; vitamins; tanning agents; skin lightening agents; antifungals; depilating agents; shaving preparations; external analgesics; perfumes; counterirritants; hemorrhoidals; insecticides; poison ivy products; poison oak products; burn products; anti- diaper rash agents; prickly heat agents; make-up preparations; vitamins; amino acids and their derivatives; herbal extracts; retinoids; flavenoids; sensates; anti-oxidants; skin conditioners; hair lighteners; chelating agents; cell turnover enhancers; coloring agents; pigments; sunscreens and mixtures thereof.

31. The system of claim 29, wherein the benefit agent is selected from the group consisting of feverfew, centella asiatica, olive leaf, wheat protein, oat oil, lycopene, DMAE, soy and derivatives thereof, colloidal oatmeal, sulfonated shale oil, elubiol, 6-(1-piperidinyl)-2,4-pyrimidinediamine-3-oxide, finasteride, ketoconazole, salicylic acid, zinc pyrithione, coal tar, benzoyl peroxide, selenium sulfide, hydrocortisone, sulfur, menthol, pramoxine hydrochloride, tricetylammonium chloride, polyquaternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, retinol, erthromycin, tretinoin, and mixtures thereof.

32. The system of claim 29, wherein the benefit agent is present in an amount, based upon the total weight of the system, from about 0.001 percent to about 5.0 percent.

33. The system of claim 24, further comprising a stability enhancer selected rom a nonionic emulsifier, an essentially non-foaming surfactant, and mixtures thereof.

34. A method of treating hair loss comprising topically applying the system of claim 24, with an effective amount of a hair loss treatment agent to a desired location on an animal or human.

35. The method of claim 34, wherein the hair loss treatment agent is selected from the group consisting of minoxidil, 6-(I-piperdinyl)-2,4-pyrimidinediamine-3-oxide, N'-cyano-N-(tert-pentyl)-N'-3-pyridinyl-guanidine, finasteride, retinoids and derivatives thereof, ketoconazole, elubiol or mixtures thereof.

36. A method for inhibiting hair growth comprising topically applying the system of claim 24, with a hair growth inhibiting agent to a desired area on an animal or human for inhibiting hair growth.

37. The method of claim 36, wherein the hair growth inhibiting agent is selected from the group consisting of serine proteases, retinol, isotretinoin, betamethoisone, alpha-tocophenol and derivatives thereof, and mixtures thereof.

38. A method for treating acne comprising topically applying a mixture of the system of claim 24, and an effective amount of an anti-acne agent to the skin of an animal or human at a desired area.

39. The method of claim 38, wherein the anti-acne agent is selected from the group consisting of benzoyl peroxide, retinol, elubiol, antibiotics, salicylic acid, and mixtures thereof.

40. A method for reducing the signs of aging and other manifestations of photodamage comprising topically applying a mixture of the system of claim 24 and an effective amount of an anti-aging agent to the skin of an animal or human at a desired area.

41. The method of claim 40, wherein the anti-aging agent is selected from the group consisting of retinoids, antioxidants, alpha-hydroxy acids, beta-hydroxy acids and mixtures thereof.

42. A method for depigmenting the skin comprising topically applying the system of claim 24 effective amount of a depigmentation benefit agent to the skin of an animal or human at a desired area.

43. The method of claim 42, wherein the depigmentation agent is selected from the group consisting of retinol, Kojic acid, hydroquinone, and mixtures thereof.

44. A method for treating the symptoms and/or the diseases of dandruff, seborrheic dermatitis and/or psoriasis, comprising topically applying a mixture of the system of claim 24 and an effective amount of a benefit agent capable of treating the symptoms to the skin of an animal or human at a desired area.

45. The method of claim 44, wherein the benefit agent is selected from the group consisting of shale oil and derivatives thereof, elubiol, ketoconazole, coal tar, salicylic acid, zinc pyrithione, selenium sulfide, hydrocortisone, sulfur, menthol, pramoxine hydrochloride, and mixtures thereof.

46. The system of claim 24, wherein said system is in the form of a gel, a bath, a wash, a mousse, a shampoo, a rinse, a lotion, a cream, a spray, or applied onto a delivery implement selected from a dry wipe, a wet wipe, a brush, or a sponge.

47. The system of claim 24, wherein said system is in the form of an oil-in-water emulsion.

48. A method of delivering a benefit agent to hair, skin or nails comprised of applying the composition of claim 29 to a desired location.

49. The system of claim 29, wherein the benefit agent is tretinoin.

* * * * *